United States Patent
Ogura et al.

(10) Patent No.: US 6,517,493 B2
(45) Date of Patent: Feb. 11, 2003

(54) SUPERIOR-AND-INFERIOR-LIMB BLOOD-PRESSURE INDEX MEASURING APPARATUS AND INFERIOR-LIMB BLOOD-PRESSURE MEASURING APPARATUS

(75) Inventors: Toshihiko Ogura, Inuyama (JP); Hidenori Suzuki, Nagoya (JP); Tomohiro Nunome, Komaki (JP)

(73) Assignee: Colin Corporation, Komaki (JP)

(*) Notice: Subject to any disclaimer, the term of this patent is extended or adjusted under 35 U.S.C. 154(b) by 0 days.

(21) Appl. No.: 09/969,605

(22) Filed: Oct. 4, 2001

(65) Prior Publication Data

US 2002/0026120 A1 Feb. 28, 2002

Related U.S. Application Data

(62) Division of application No. 09/559,827, filed on Apr. 28, 2000.

(30) Foreign Application Priority Data

May 17, 1999 (JP) .............................. 11-135928

(51) Int. Cl.[7] ............................................ A61B 5/02
(52) U.S. Cl. ................ 600/490; 600/492; 600/494; 600/485
(58) Field of Search ............................ 600/481, 490, 600/485, 492, 493, 494, 495, 496, 497, 498, 499, 500, 501, 502, 503

(56) References Cited

U.S. PATENT DOCUMENTS

| 4,819,654 A | 4/1989 | Weaver et al. |
| 5,101,828 A | 4/1992 | Welkowitz et al. |
| 5,261,414 A | 11/1993 | Aung et al. |
| 5,265,011 A | 11/1993 | O'Rourke |
| 5,715,826 A | 2/1998 | Horrocks et al. |
| 5,743,857 A | 4/1998 | Shinoda et al. |
| 5,830,149 A | 11/1998 | Oka et al |
| 5,836,888 A | 11/1998 | Ogura et al. |
| 6,346,083 B1 * | 3/2002 | Nishibayashi et al. ...... 600/490 |
| 6,355,000 B1 * | 3/2002 | Ogura .......................... 600/490 |

* cited by examiner

Primary Examiner—Max F. Hindenburg
Assistant Examiner—Navin Natnithithadha
(74) Attorney, Agent, or Firm—Oliff & Berridge, PLC

(57) ABSTRACT

An apparatus for measuring a superior-and-inferior-limb blood-pressure index of a living subject, including a first blood-pressure measuring device which measures a first blood pressure of a right inferior limb of the subject, a second blood-pressure measuring device which measures a second blood pressure of a left inferior limb of the subject, a third blood-pressure measuring device which measures a third blood pressure of a superior limb of the subject, a first information obtaining device which obtains first information relating to a first velocity of propagation of a first pulse wave which propagates through a first route a portion of which runs in the right inferior limb, a second information obtaining device which obtains second information relating to a second velocity of propagation of a second pulse wave which propagates through a second route a portion of which runs in the left inferior limb, a selecting device for selecting one of the measured first and second blood pressures that corresponds to one of the first and second information that relates to a lower one of the first and second velocities, and an index determining device for determining the superior-and-inferior-limb blood-pressure index, based on the selected one of the first and second blood pressures, and the measured third blood pressure.

5 Claims, 11 Drawing Sheets

SUPERIOR-AND-INFERIOR-LIMB BLOOD-PRESSURE INDEX MEASURING APPARATUS AND INFERIOR-LIMB BLOOD-PRESSURE MEASURING APPARATUS

This is a Division of application Ser. No. 09/559,827 filed Apr. 28, 2000. The entire disclosure of the prior application(s) is hereby incorporated by reference herein in its entirety.

BACKGROUND OF THE INVENTION

1. Field of the Invention

The present invention relates to an apparatus for measuring a superior-and-inferior-limb blood-pressure index of a living subject (e.g., a ratio of an inferior-limb blood pressure to a superior-limb blood pressure, or a ratio of a superior-limb blood pressure to an inferior-limb blood pressure), and to an apparatus for measuring a blood pressure of an inferior limb of a living subject, the latter apparatus being advantageously employed by the former apparatus.

2. Related Art Statement

For a person who suffers arterial obstruction or arteriostenosis, his or her inferior-limb blood pressure ("BP") value is lower than his or her corresponding superior-limb BP value (for example, a systolic superior-limb BP value corresponds to a systolic inferior-limb BP value). Meanwhile, if an inferior-limb BP value of a person is higher than his or her corresponding superior-limb BP value by a prescribed value, he or she may suffer aortic incompetence or aortitis syndrome limited to aortic arch. It has been practiced to utilize this for diagnosing arterial disease based on the ratio of inferior-limb BP value to superior-limb BP value or the ratio of superior-limb BP value to inferior-limb BP value, that is, a superior-and-inferior-limb BP index.

Since the superior-and-inferior-limb BP index is simply obtained as the ratio of inferior-limb BP value-to superior-limb BP value or the ratio of superior-limb BP value to inferior-limb BP value, it is required to measure accurately the inferior-limb BP value. However, if one or more blood vessels running in a portion of an inferior limb from which the inferior-limb BP value is measured suffer advanced calcification, that is, sclerosis of tunica media as the middle one of three layers of tunica vasculosa, the inferior-limb BP value is raised because of the hardness of the blood vessels. In addition, since an inferior limb is thicker than a superior limb and has a generally conical shape, it is hard to wind an inflatable cuff around it. Moreover, since arterial vessels running in an inferior limb are present deep in adipose tissues and muscles, it is naturally harder to measure an inferior-limb BP value than measure a superior-limb BP value. In the case where blood vessels running in a portion of an inferior limb from which an inferior-limb BP value is measured suffer highly advanced calcification, those blood vessels cannot be fully occluded by the pressing of an inflatable cuff and accordingly an excessively high inferior-limb BP value may be measured. Therefore, if a person who suffers arterial obstruction or arteriostenosis also suffers advanced calcification of his or her inferior-limb blood vessels, a normal superior-and-inferior-limb BP index value may be measured from the person. In this case, arterial obstruction or arterio-stenosis cannot be accurately diagnoses based on the superior-and-inferior-limb BP index.

SUMMARY OF THE INVENTION

It is therefore an object of the present invention to provide an apparatus which can measure a highly reliable superior-and-inferior-limb blood-pressure index of a living subject even if he or she may suffer the calcification of his or her inferior-limb blood vessels.

It is another object of the present invention to provide an apparatus which measures a superior-and-inferior-limb blood-pressure index of a living subject while judging whether the measurement of an inferior-limb blood pressure is abnormal.

It is another object of the present invention to provide an apparatus which measures an inferior-limb blood-pressure of a living subject while judging whether the subject suffers the calcification of his or her inferior-limb blood vessel.

(1) According to a first feature of the present invention, there is provided an apparatus for measuring a superior-and-inferior-limb blood-pressure index of a living subject, comprising a first blood-pressure measuring device which measures a first blood pressure of a right inferior limb of the subject; a second blood-pressure measuring device which measures a second blood pressure of a left inferior limb of the subject; a third blood-pressure measuring device which measures a third blood pressure of a superior limb of the subject; a first information obtaining device which obtains first information relating to a first velocity of propagation of a first pulse wave which propagates through a first route a portion of which runs in the right inferior limb; a second information obtaining device which obtains second information relating to a second velocity of propagation of a second pulse wave which propagates through a second route a portion of which runs in the left inferior limb; selecting means for selecting one of the measured first and second blood pressures that corresponds to one of the first and second information that relates to a lower one of the first and second velocities; and index determining means for determining the superior-and-inferior-limb blood-pressure index, based on the selected one of the first and second blood pressures, and the measured third blood pressure.

According to this feature, the first information obtaining device obtains first information relating to a first velocity of propagation of a first pulse wave which propagates through a first route a portion of which runs in the right inferior limb, the second information obtaining device obtains second information relating to a second velocity of propagation of a second pulse wave which propagates through a second route a portion of which runs in the left inferior limb, the selecting means selects one of the measured first and second BP values that corresponds to one of the first and second information that relates to a lower one of the first and second velocities, and the index determining means determines the superior-and-inferior-limb BP index, based on the selected one of the first and second BP values, and the measured third BP value. The higher the degree of calcification of blood vessel is, the higher the velocity of propagation of pulse wave through the blood vessel is. Therefore, the selected one of the measured first and second BP values that corresponds to the lower one of the first and second velocities, means the inferior-limb BP value measured from the less calcified inferior limb. Since this inferior-limb BP value, selected by the selecting means, is used in determining the superior-and-inferior-limb BP index, a highly reliably superior-and-inferior-limb BP index value can be obtained.

(2) According to a second feature of the present invention that includes the first feature (1), the index determining means comprises means for determining, as the superior-and-inferior-limb blood-pressure index, a ratio of the selected one of the first and second blood pressures to the third blood pressure, or a ratio of the third blood pressure to the selected one of the first and second blood pressures.

(3) According to a third feature of the present invention that includes the first or second feature (1) or (2), the first information obtaining device comprises two first pulse-wave sensors which are worn on two different first portions of the living subject, respectively, and each of which detects the first pulse wave at a corresponding one of the two first portions, at least one of the two first portions belonging to the right inferior limb, and the second information obtaining device comprises two second pulse-wave sensors which are worn on two different second portions of the subject, respectively, and each of which detects the second pulse wave at a corresponding one of the two second portions, at least one of the two second portions belonging to the left inferior limb.

(4) According to a fourth feature of the present invention that includes the third feature (3), the first information obtaining device comprises first time determining means for determining, based on respective times when the two first pulse-wave sensors detect the first pulse wave, a first propagation time needed for the first pulse wave to propagate between the two different first portions of the living subject, and the second information obtaining device comprises second time determining means for determining, based on respective times when the two second pulse-wave sensors detect the second pulse wave, a second propagation time needed for the second pulse wave to propagate between the two different second portions of the subject.

(5) According to a fifth feature of the present invention that includes the fourth feature (4), the first information obtaining device comprises first velocity determining means for determining, based on the determined first propagation time and a distance between the two first portions of the living body, the first velocity of propagation of the first pulse wave, and wherein the second information obtaining device comprises second velocity determining means for determining, based on the determined second propagation time and a distance between the two second portions of the living body, the second velocity of propagation of the second pulse wave.

(6) According to a sixth feature of the present invention, there is provided an apparatus for measuring a superior-and-inferior-limb blood-pressure index of a living subject, comprising a first blood-pressure measuring device which includes a first inflatable cuff adapted to be wound around an inferior limb of the subject and which measures a first blood pressure of the inferior limb; a second blood-pressure measuring device which measures a second blood pressure of a superior limb of the subject; a first pulse-wave sensor which detects a first pulse wave which propagates through a portion of the inferior limb that is located on an upstream side of the first inflatable cuff; sharpness determining means for determining a degree of sharpness of a heartbeat-synchronous pulse of the first pulse wave detected by the first pulse-wave sensor; and judging means for judging that when the determined degree of sharpness is not greater than a first reference value and the measured first blood pressure is higher than the measured second blood pressure by a value not smaller than a second reference value, the measurement of the first blood pressure by the first blood pressure measuring device is abnormal.

According to this feature, the sharpness determining means determines a degree of sharpness of a heartbeat-synchronous pulse of the first pulse wave detected by the first pulse-wave sensor, and the judging means judges that when the determined degree of sharpness is not greater than a first reference value and the measured first blood pressure is higher than the measured second blood pressure by a value not smaller than a second reference value, the measurement of the first-blood pressure by the first blood pressure measuring device is abnormal. Thus, an operator such as a medical staff can recognize that the measurement of the first blood pressure has not been properly performed by the first blood pressure measuring device. A small degree of sharpness, determined by the sharpness determining means, means that the subject suffers arteriostenosis in the portion of the inferior limb located on the upstream side of the first inflatable cuff and accordingly a lowered BP value is measured from a portion of the inferior limb located on a downstream side of the cuff. If it is assumed that the BP measurement has been properly performed, the determined degree of sharpness which is not greater than the first reference value should mean that the measured inferior-limb BP value is equal to, or lower than the superior-limb BP value. When, in fact, the measured inferior-limb BP value is higher than the superior-limb BP value by a value not smaller than the second reference value, it can therefore be concluded that the BP measurement was abnormal because the blood blow through the blood vessel or vessels running in the portion of the inferior limb pressed by the cuff cannot be fully stopped by the cuff.

(7) According to a seventh feature of the present invention that includes the sixth feature (6), the second blood-pressure measuring device comprises a second inflatable cuff adapted to be wound around the superior limb of the subject, and wherein the apparatus further comprises a second pulse-wave sensor which detects a second pulse wave which propagates through a portion of the superior limb that is located on an upstream side of the second inflatable cuff; and reference-value determining means for determining the first reference value based on the second pulse wave detected by the second pulse-wave sensor.

(8) According to an eighth feature of the present invention that includes the sixth or seventh feature (6) or (7), the sharpness determining means comprises means for determining, as the degree of sharpness, a percentage, %MAP, of a height of a center of gravity of an area enveloped by a waveform of the heartbeat-synchronous pulse of the first pulse wave, relative to an amplitude of the waveform of the pulse.

(9) According to a ninth feature of the present invention, there is provided an apparatus for measuring a superior-and-inferior-limb blood-pressure index of a living subject, comprising a first blood-pressure measuring device which includes an inflatable cuff adapted to be wound around an inferior limb of the subject and which measures a first blood pressure of the inferior limb; a second blood-pressure measuring device which measures a second blood pressure of a superior limb of the subject; a first pulse-wave sensor which detects a first pulse wave which propagates through a portion of the inferior limb that is located on an upstream side of the inflatable cuff; a second pulse-wave sensor which detects a second pulse wave which propagates through the superior limb; and a display device which simultaneously displays the measured first and second blood pressures and the detected first and second pulse waves.

According to this feature, the display device simultaneously displays the measured first and second blood pressures and the detected first and second pulse waves. Therefore, if the first or inferior-limb BP value is higher than the second or superior-limb BP value but an observer can see on the display device that the first or inferior-limb pulse wave is less sharp than the second or superior-limb pulse wave, the observer can judge that the BP measurement peformed by the first or inferior-limb BP measuring device was abnormal.

(10) According to a tenth feature of the present invention that includes the ninth feature (9), the apparatus further comprises index determining means for determining a superior-and-inferior-limb blood-pressure index of the subject, based on the measured first and second blood pressures, and the display device displays the determined superior-and-inferior-limb blood-pressure index, in addition to the measured first and second blood pressures and the detected first and second pulse waves.

(11) According to an eleventh feature of the present invention, there is provided an apparatus for measuring a blood pressure of an inferior limb of a living subject, comprising a blood-pressure measuring device which includes an inflatable cuff adapted to be wound around the inferior limb and which measures, with the cuff, the blood pressure of the inferior limb of the subject; an input device which is operable for inputting at least one characteristic value characteristic of the subject and which produces at least one signal representing the at least one input characteristic value; map selecting means for selecting, based on the input characteristic value, one of a plurality of predetermined maps each of which defines, in a coordinate system having a first axis representing blood pressure and a second axis representing information relating to velocity of propagation of pulse wave through blood vessel, a calcification range indicating calcification of the blood vessel; an information obtaining device which obtains information relating to a velocity of propagation of a pulse wave which propagates between two different portions of the subject that include a portion of the inferior limb around which the inflatable cuff is wound; and judging means for judging whether the measured blood pressure and the obtained information fall in the calcification range of the selected map, and thereby judging whether at least one blood vessel running in the portion of the inferior limb has been calcified to such a degree that a blood flow through the blood vessel cannot be stopped by the inflatable cuff.

According to this feature, the map selecting means selects, based on the input characteristic value, one of a plurality of predetermined maps each of which defines, in a coordinate system having a first axis representing blood pressure and a second axis representing information relating to velocity of propagation of pulse wave through blood vessel, a calcification range indicating calcification of the blood vessel, and the judging means judges whether the measured blood pressure and the obtained information fall in the calcification range of the selected map, and thereby judges whether at least one blood vessel running in the portion of the inferior limb has been calcified to such a degree that a blood flow through the blood vessel cannot be stopped by the inflatable cuff. Therefore, an operator can recognize that the BP measurement performed by the BP measuring device was abnormal.

(12) According to a twelfth feature of the present invention that includes the eleventh feature (11), the input device comprises means for inputting, as the at least one characteristic value, at least one value selected from the group consisting of an age of the subject, a value corresponding to a sex of the subject, and a height of the subject.

(13) According to a thirteenth feature of the present invention that includes the eleventh or twelfth feature (11) or (12), the apparatus further comprises a memory which stores the plurality of predetermined maps.

(14) According to a fourteenth feature of the present invention that includes any one of the eleventh to thirteenth features (11) to (13), the information obtaining device comprises propagation-time measuring means for measuring a time needed for the pulse wave to propagate between the two different portions of the subject.

(15) According to a fifteenth feature of the present invention that includes the fourteenth feature (14), the information obtaining device further comprises inverse-of-propagation-time determining means for determining, as the information, an inverse of the propagation time measured by the propagation-time measuring means.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
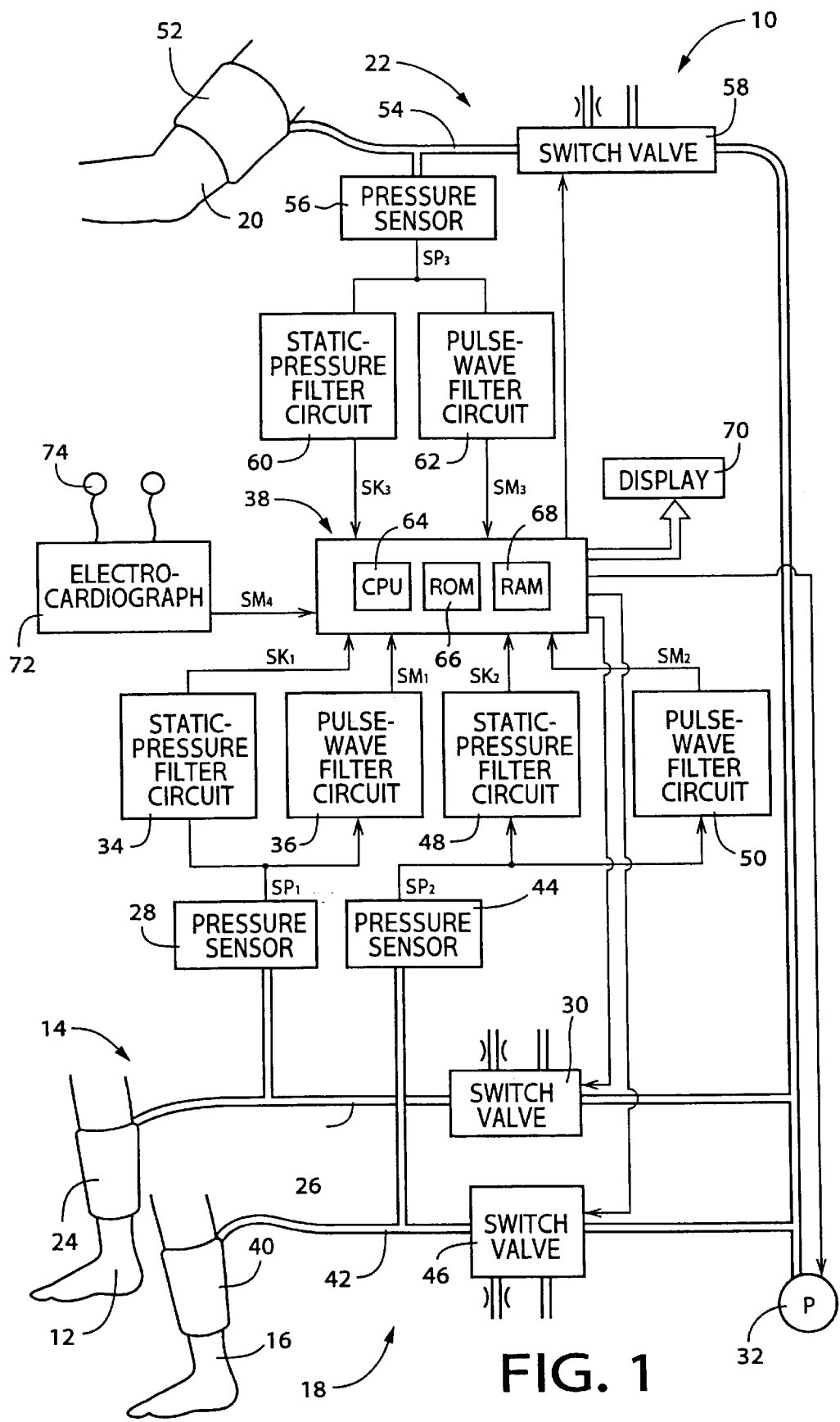
FIG. 1 is a diagrammatic view of the construction of an ankle/arm blood-pressure ("BP") index measuring apparatus to which the present invention is applied.

Hereinafter, there will be described an ankle/arm blood-pressure ("BP") index measuring apparatus 10 to which the present invention is applied, by reference to the drawings. FIG. 1 is a block diagram showing the construction of the measuring apparatus 10. The ankle/arm BP index measuring apparatus 10 is a sort of superior-and-inferior-limb BP index measuring apparatus, since the measuring apparatus 10 measures, as an inferior-limb BP value, a BP value from an ankle of a patient as a living person and measures, as a superior-limb BP value, a BP value from an upper arm of the patient. The present apparatus 10 carries out the BP measurements on the patient who takes the face-down, lateral, or face-up position so that the upper arm and the ankle are substantially level with each other.

In FIG. 1, the ankle/arm BP index measuring apparatus 10 includes a right-ankle BP measuring device 14 which measures a BP value from a right ankle 12 of the patient, a left-ankle BP measuring device 18 which measures a BP value from a left ankle 16 of the patient, and an upper-arm BP measuring device 22 which measures a BP value from an upper arm 20 of the patient.

The right-ankle BP measuring device 14 includes an inflatable cuff 24 which includes a belt-like cloth bag and a rubber bag accommodated in the cloth bag and which is wound around the right ankle 12 of the patient; a piping 26; and a pressure sensor 28, a switch valve 30, and an air pump 32 which are connected to the cuff 24 via the piping 26. The switch valve 30 is selectively placed in one of three operation states, that is, (a) a pressurized-air-supply state in which the switch valve 30 allows pressurized air to be supplied from the air pump 32 to the cuff 24, (b) a slow-deflation state in which the valve 30 allows the pressurized air to be deflated slowly from the cuff 24, and (c) a quick-deflation state in which the valve 30 allows the pressurized air to be deflated quickly from the cuff 24.

The pressure sensor 28 detects an air pressure in the cuff 24, and supplies a pressure signal, $SP_1$, representing the detected air pressure, to a static-pressure filter circuit 34 and a pulse-wave filter circuit 36. The static-pressure filter circuit 34 includes a low-pass filter which allows only low frequencies to pass therethrough and thereby selects, from the pressure signal $SP_1$, a cuff-pressure signal, $SK_1$, representing a cuff pressure, $P_{C1}$, as the constant component of the detected air pressure. The filter circuit 34 supplies the cuff-pressure signal $SK_1$ to an electronic control device 38 via an analog-to-digital ("A/D") converter (not shown).

The pulse-wave filter circuit 36 includes a band-pass filter which allows only specific frequencies to pass therethrough and thereby selects, from the pressure signal $SP_1$, a pulse-wave signal, $SM_1$, representing a pulse wave as the oscillatory component of the detected air pressure. The filter circuit 36 supplies the pulse-wave signal $SM_1$ to the electronic control device 38 via an A/D converter (not shown).

The left-ankle BP measuring device 18 includes an inflatable cuff 40, a piping 42, a pressure sensor 44, and a switch valve 46 which have respective constructions identical with those of the counterparts 24, 26, 28, 30 of the right-ankle BP measuring device 14. The cuff 40 of the left-ankle BP measuring device 18 is wound around a portion of the left ankle 16 that corresponds to a portion of the right ankle 12 around which the cuff 24 of the right-ankle BP measuring device 14 is wound. The switch valve 46 is connected to the air pump 32. The pressure sensor 44 detects an air pressure in the cuff 40, and supplies a pressure signal, $SP_2$, representing the detected air pressure, to a static-pressure filter circuit 48 and a pulse-wave filter circuit 50 which have respective constructions identical with those of the counterparts 34, 36 of the right-ankle BP measuring device 14. The static-pressure filter circuit 48 selects, from the pressure signal $SP_2$, a cuff-pressure signal, $SK_2$, representing a cuff pressure, $P_{C2}$, as the constant component of the detected air pressure, and supplies the cuff-pressure signal $SK_2$ to the control device 38 via an A/D converter (not shown). The pulse-wave filter circuit 50 selects, from the pressure signal $SP_2$, a pulse-wave signal, $SM_2$, representing a pulse wave as the oscillatory component of the detected air pressure, and supplies the pulse-wave signal $SM_2$ to the control device 38 via an A/D converter (not shown).

The upper-arm BP measuring device 22 includes an inflatable cuff 52 which has a construction identical with the cuff 24 or 40 and which is wound around an upper arm 20 (e.g., a right upper arm) of the patient; and a piping 54, a pressure sensor 56, and a switch valve 58 which have respective constructions identical with those of the counterparts 24, 26, 28, 30 of the right-ankle BP measuring device 14. The switch valve 58 is connected to the air pump 32. The pressure sensor 56 detects an air pressure in the cuff 52, and supplies a pressure signal, $SP_3$, representing the detected air pressure, to a static-pressure filter circuit 60 and a pulse-wave filter circuit 62 which have respective constructions identical with those of the counterparts 34, 36 of the right-ankle BP measuring device 14. The static-pressure filter circuit 60 selects, from the pressure signal $SP_3$, a cuff-pressure signal, $SK_3$, representing a cuff pressure, $P_{C3}$, as the constant component of the detected air pressure, and supplies the cuff-pressure signal $SK_3$ to the control device 38 via an A/D converter (not shown). The pulse-wave filter circuit 62 selects, from the pressure signal $SP_3$, a pulse-wave signal, $SM_3$, representing a pulse wave as the oscillatory component of the detected air pressure, and supplies the pulse-wave signal $SM_3$ to the control device 38 via an A/D converter (not shown).

The electronic control device 38 is essentially provided by a microcomputer including a central processing unit ("CPU") 64, a read-only memory ("ROM") 66, a random access memory ("RAM") 68, and an input-and-output ("I/O") port (not shown), and processes input signals according to control programs pre-stored in the ROM 66, while utilizing the temporary-storage function of the RAM 68. The control device 38 outputs, from the I/O port, drive signals to the air pump 32 and the three switch valves 30, 46, 58 so as to control the respective operations thereof, and display signals to a display device 70 so as to control the contents displayed thereby.

Figure 3:
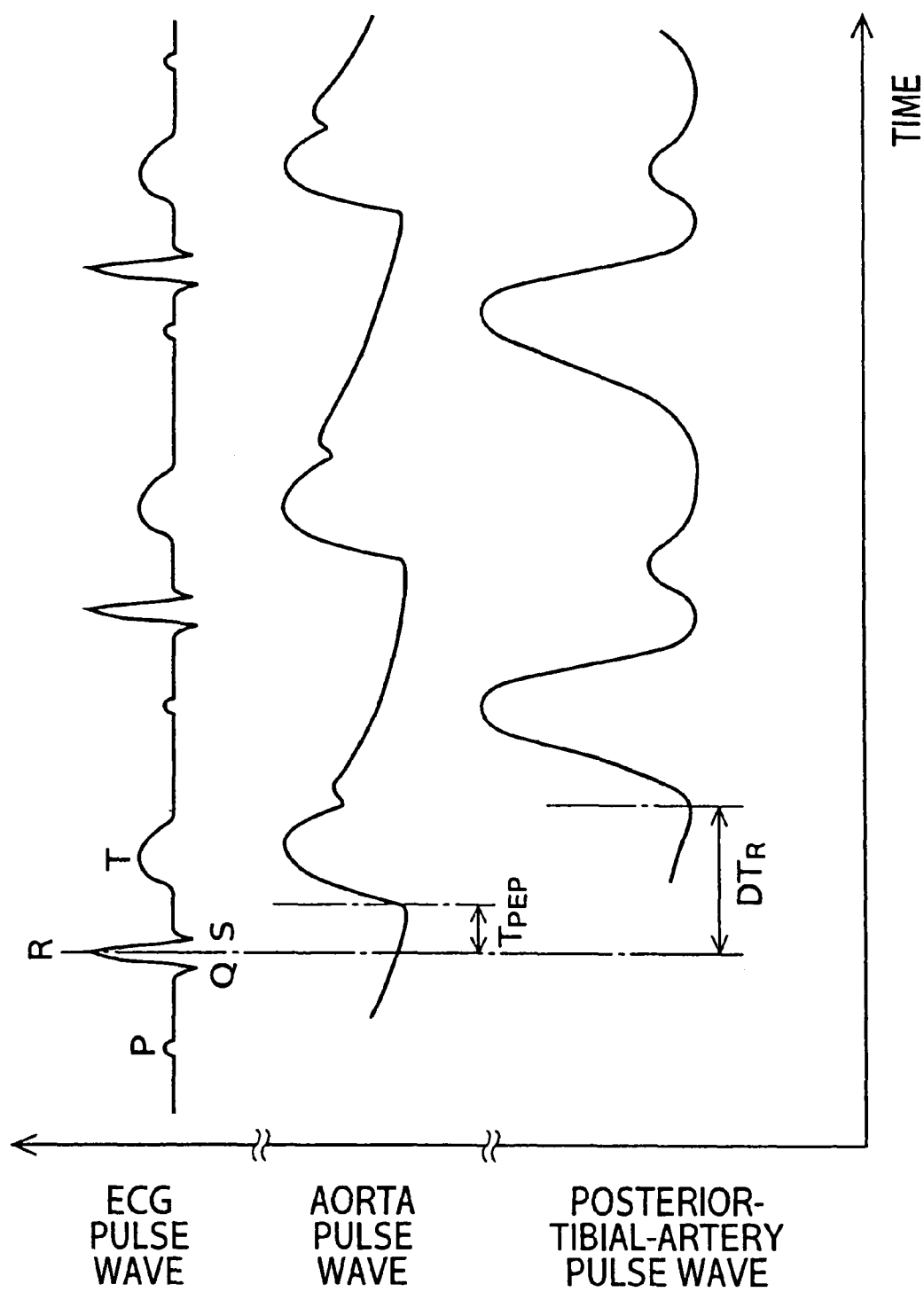
FIG. 3 is a view showing an example of a right pulse-wave propagation time, $DT_R$, determined by the operation of the control device of the measuring device of FIG. 1.

An electrocardiograph ("ECG") 72 includes a plurality of electrodes 74 adapted to be attached to predetermined portions of the patient, and continuously detects an electrocardiogram representing the active potential of the heart muscle of the patient. The ECG 72 supplies an ECG signal, $SM_4$, representing the detected electrocardiogram, to the electronic control device 38. The electrocariogram detected by the ECG 72 includes, as shown in FIG. 3, a Q wave or an R wave that corresponds to a time when the heart starts outputting blood toward the aorta. Thus, the ECG 72 functions as a first pulse-wave sensor.

Figure 2:
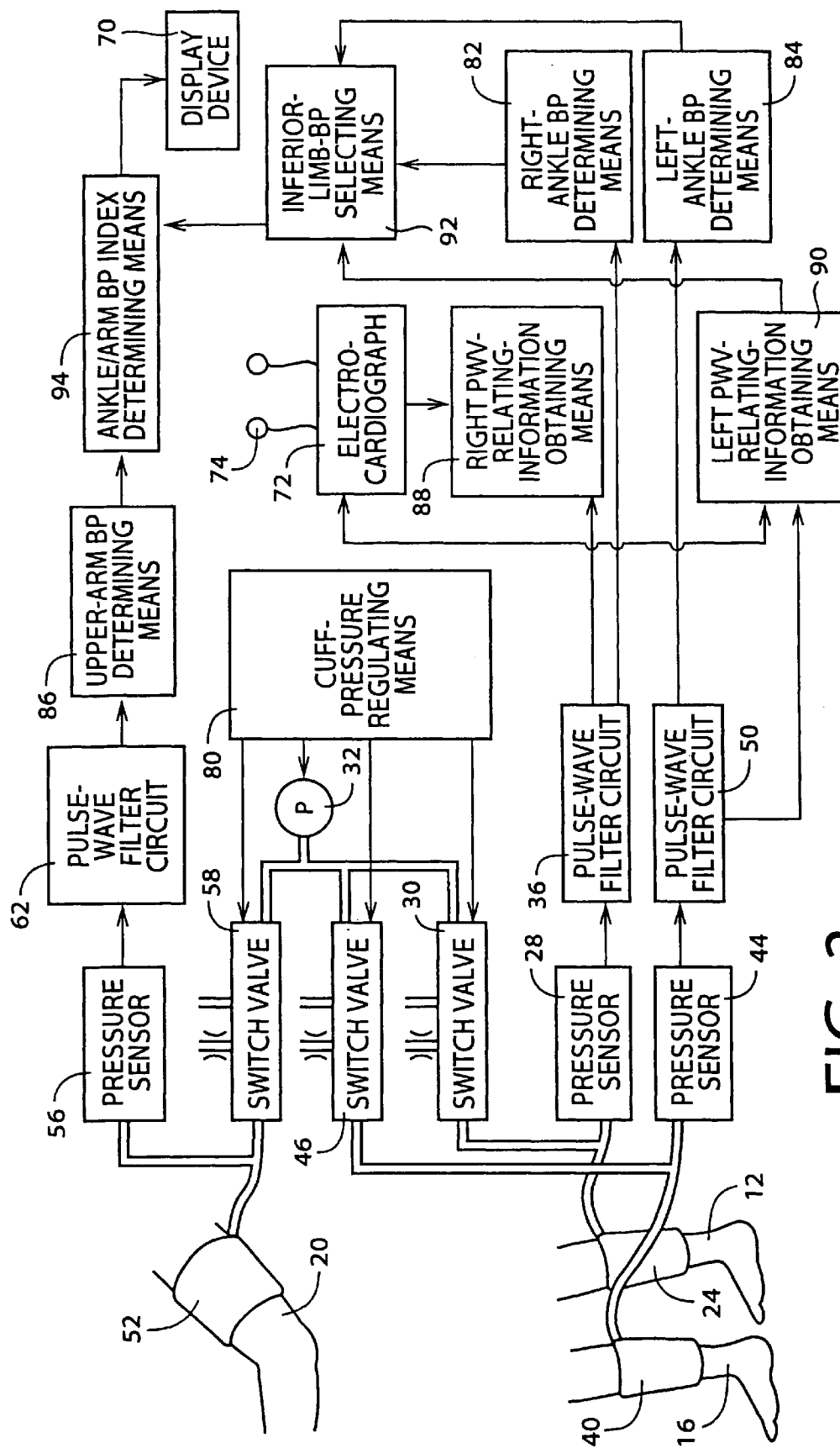
FIG. 2 is a diagrammatic view of important control functions of an electronic control device of the measuring apparatus of FIG. 1.

FIG. 2 is a diagrammatic view for explaining the important control functions of the control device 38. A cuff-pressure regulating means 80 controls, in each BP measuring operation, the air pump 32 and the three switch valves 30, 46, 58 each connected thereto, such that the respective pressing pressures of the three cuffs 24, 40, 52 are quickly increased up-to a predetermined target pressure value, $P_{CM}$, (e.g., about 180 mmHg) and then are slowly decreased at a rate of about 3 mmHg/sec. In each pulse-wave detecting operation carried out for obtaining information relating to velocity of propagation of pulse wave, the cuff-pressure regulating means 80 controls the air pump 32 and the two switch valves 30, 46 each connected thereto, such that the respective pressing pressures $P_{C1}$, $P_{C2}$ of the two cuffs 24, 40 are quickly increased up to a predetermined target pressure value which is sufficiently lower than a diastolic BP value of the patient, and then are maintained at the target pressure for a predetermined time duration.

A right-ankle BP determining means 82 determines right-ankle systolic and diastolic BP values, $BP_{RSYS}$, $BP_{RDIA}$, etc., that is, BP values of the right ankle 12, according to well-known oscillometric method, based on the change of respective amplitudes of the heartbeat-synchronous pulses of the pulse-wave signal SM$_1$ detected one by one during the slow deflation of the cuff 24 wound around the right ankle 12 under the control of the cuff-pressure regulating means 80.

A left-ankle BP determining means 84 determines left-ankle systolic and diastolic BP values, BP$_{LSYS}$, BP$_{LDIA}$, etc., that is, BP values of the left ankle 16, according to the oscillometric method, based on the change of respective amplitudes of the heartbeat-synchronous pulses of the pulse-wave signal SM$_2$ detected one by one during the slow deflation of the cuff 40 wound around the left ankle 16 under the control of the cuff-pressure regulating means 80.

An upper-arm BP determining means 86 determines upper-arm systolic and diastolic BP values, BP$_{ASYS}$, BP$_{ADIA}$, etc., that is, BP values of the upper arm 20, according to the oscillometric method, based on the change of respective amplitudes of the heartbeat-synchronous pulses of the pulse-wave signal SM$_3$ detected one by one during the slow deflation of the cuff 52 wound around the upper arm 20 under the control of the cuff-pressure regulating means 80.

A right pulse-wave-propagation-velocity ("PWV") relating information obtaining means 88 obtains information relating to a velocity of propagation of a pulse wave which propagates through a right pulse-wave propagation route including a portion thereof running in the right inferior limb. More specifically, the right PWV-relating-information obtaining means 88 obtains information relating to a velocity of propagation of a pulse wave between two portions of the patient, based on a second pulse wave detected by a right second pulse-wave sensor worn on a portion of the right inferior limb that is located on an upstream side of the cuff 24 wound around the right ankle 12, i.e., on a proximal side of the cuff 24 (this upstream-side portion of the right inferior limb may be a portion thereof around which the cuff 24 is wound), and a first pulse wave detected by a right first pulse-wave sensor worn on a proximal side of the right second pulse-wave sensor. For example, the right PWV-relating-information obtaining means 88 determines, as the right PWV-relating information, a right PWV value, V$_R$, or a right pulse-wave propagation time, DT$_R$, based on a time difference between a periodic point on each of heartbeat-synchronous pulses of the first pulse wave, and a periodic point on a corresponding one of heartbeat-synchronous pulses of the second pulse wave. The ECG 72 functions as the right first pulse-wave sensor, and the pulse-wave filter circuit 36 of the right-ankle BP measuring device 14 that detects a pulse wave from the posterior tibial artery running in the portion of the right ankle 12 around which the cuff 24 is wound, functions as the second pulse-wave sensor. The right PWV-relating-information obtaining means 88 includes a time-difference calculating means which calculates a time difference (i.e., right pulse-wave propagation time), DT$_R$, shown in FIG. 3, that is, a time difference between a time point at which the ECG 72 detects the R wave of each heartbeat-synchronous pulse of the electrocardiogram (i.e., ECG waveform), and a time point at which the filter circuit 36 detects the rising point (i.e., the lowest point) of a corresponding heartbeat-synchronous pulse of the posterior-tibial-artery pulse wave. The right PWV-relating-information obtaining means 88 iteratively calculates, based on the calculated time difference DT$_R$ calculated by the time-difference calculating means for each of the heartbeat-synchronous pulses, a right PWV value V$_R$ (m/sec), according to the following expression (1) pre-stored in the RON 66:

$$V_R = L_R/(DT_R - T_{PEP}) \quad (1)$$

where L$_R$ (m) is the distance from the left ventricle of the heart, via the aorta, to the portion of the right ankle 12 around which the cuff 24 is wound; and T$_{PEP}$ (sec) is a pre-ejection time between the R wave of the ECG waveform and the rising point of the aortic pulse wave, as shown in FIG. 3 (L$_R$ and T$_{PEP}$ are replaced with respective constant values which are experimentally obtained in advance).

Like the right PWV-relating-information obtaining means 88, a left PWV-relating-information obtaining means 90 obtains information relating to a velocity of propagation of a pulse wave which propagates through a left pulse-wave propagation route including a portion thereof running in the left inferior limb. More specifically, the left PWV-relating-information obtaining means 90 obtains information relating to a velocity of propagation of a pulse wave between two portions of the patient, based on a second pulse wave detected by a left second pulse-wave sensor worn on a portion of the left inferior limb that is located on an upstream side of the cuff 40 wound around the left ankle 16, i.e., on a proximal side of the cuff 40 (the upstream-side portion of the left inferior limb may be a portion thereof around which the cuff 40 is wound), and a first pulse wave detected by a left first pulse-wave sensor worn on a proximal side of the left second pulse-wave sensor. The left first and second pulse-wave sensors are worn on the patient, symmetrically with the right first and second pulse-wave sensors, with respect to the centerline of the patient. Thus, the distance between the cuff 40 and each of the left first and second pulse-wave sensors is equal to the distance between the cuff 24 and a corresponding one of the right first and second pulse-wave sensors. The ECG 72 functioning as the right first pulse-wave sensor also functions as the left first pulse-wave sensor, and the pulse-wave filter circuit 50 of the left-ankle BP measuring device 18 functions as the left second pulse-wave sensor. The left PWV-relating-information obtaining means 90 includes a time-difference calculating means which calculates a time difference (i.e., left pulse-wave propagation time), DT$_L$, that is, a time difference between a time point at which the ECG 72 detects the R wave of each heartbeat-synchronous pulse of the ECG waveform, and a time point at which the filter circuit 50 detects the rising point (i.e., the lowest point) of a corresponding heartbeat-synchronous pulse of the posterior-tibial-artery pulse wave. The left PWV-relating-information obtaining means 90 iteratively calculates, based on the calculated time difference DT$_L$ calculated by the time-difference calculating means for each of the heartbeat-synchronous pulses, a left PWV value V$_R$ (m/sec), according to the following expression (2) pre-stored in the ROM 66:

$$V_L = L_L/(DT_L - T_{PEP}) \quad (2)$$

where L$_L$ (m) is the distance from the left ventricle of the heart, via the aorta, to the portion of the left ankle 16 around which the cuff 40 is wound. (L$_L$ is replaced with a constant value which is experimentally obtained in advance).

A BP selecting means 92 compares the right PWV-relating information obtained by the means 88 and the left PWV-relating information obtained by the means 90, with each other, and selects one of the right-ankle BP value BP$_R$ determined by the right-ankle BP determining means 82 and the corresponding left-ankle BP value $BP_L$ determined by the left-ankle BP determining means 84, so that the selected ankle BP value is used by an ankle/arm BP index determining means 94, described below, to determine an ankle/arm BP index ("API"). More specifically described, the selecting means 92 selects, as the ankle BP value, one of the right-ankle and left-ankle BP values $BP_R$, $BP_L$, that corresponds to the lower one of the right and left propagation velocities $V_R$, $V_L$, or the longer one of the right and left propagation times $DT_R$, $DT_L$.

An API determining means 94 determines or calculates an API value based on the inferior-limb BP value selected by the BP selecting means 92 and the corresponding upper-arm BP value $BP_A$ determined by the upper-arm BP determining means 86. For example, in the case where the BP selecting means 92 selects the right-ankle systolic BP value $BP_{RSYS}$, the API may be obtained by dividing the right-ankle systolic BP value $BP_{RSYS}$ by the upper-arm systolic BP value $BP_{ASYS}$, or dividing the upper-arm systolic BP value $BP_{ASYS}$ by the right-ankle systolic BP value $BP_{RSYS}$. The thus determined API value is displayed on the display device 70.

Figure 4:
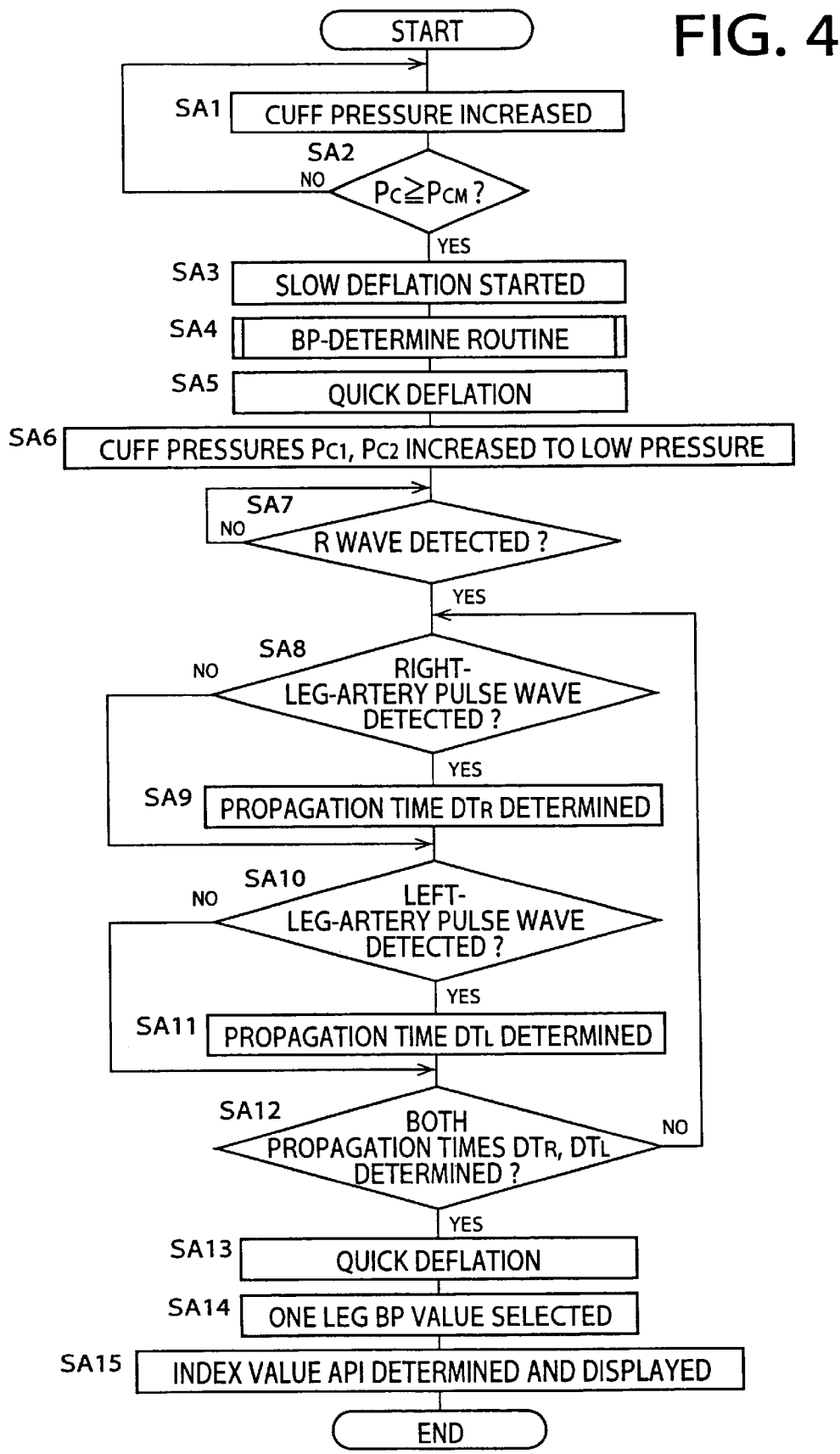
FIG. 4 is a flow chart representing a control program according to which the control device of the measuring apparatus of FIG. 1 is operated.

FIG. 4 is a flow chart representing a control program according to which the control device 38 is operated. First, the control of the control device 38 starts with Steps S1, S2, and S3 corresponding to the cuff-pressure regulating means 80. At Step SA1, the three switch valves 30, 46, 58 are switched to their pressure-supply positions and the air pump 32 is operated, so that the respective air pressures of the three cuffs 24, 40, 52 are quickly increased. At Step SA2, it is judged whether all the air pressures PC of the three cuffs 24, 40, 52 have reached the predetermined target pressure value PCM (about 180 mmHg). If a negative judgment is made at Step SA2, Steps SA1 and SA2 are repeated to continue increasing the air pressures PC of the cuffs 24, 40, 52.

If a positive judgment is made at Step SA2, the control goes to Step SA3 to stop the operation of the air pump 32 and switch the three switch valves 30, 46, 58 to their slow-deflation positions, so that the respective air pressures PC of the three cuffs 24, 40, 52 are decreased slowly at a predetermined low rate of about 3 mmHg/sec.

Step SA3 is followed by the BP-determine routine of Step SA4, corresponding to the right-ankle BP determining means 82, the left-ankle BP determining means 84, and the upper-arm BP determining means 86. More specifically described, the control device 38 determines an amplitude of each of successive heartbeat-synchronous pulses of the cuff pulse wave represented by the pulse-wave signal $SM_1$ supplied from the pulse-wave filter circuit 36, and determines a right-ankle systolic BP value $BP_{RSYS}$, etc. based on the timewise change of the thus determined amplitudes according to a well-known oscillometric BP-determine algorithm. Similarly, the control device 38 determines an amplitude of each of successive heartbeat-synchronous pulses of the cuff pulse wave represented by the pulse-wave signal $SM_2$ supplied from the pulse-wave filter circuit 50, and determines a left-ankle systolic BP value $BP_{LSYS}$, etc. based on the timewise change of the thus determined amplitudes according to the oscillometric BP-determine algorithm. In addition, the control device 38 determines an amplitude of each of successive heartbeat-synchronous pulses of the cuff pulse wave represented by the pulse-wave signal $SM_3$ supplied from the pulse-wave filter circuit 62, and determines an upper-arm systolic BP value $BP_{ASYS}$, etc. based on the timewise change of the thus determined amplitudes according to the oscillometric BP-determine algorithm.

Step SA4 is followed by Step SA5 corresponding to the cuff-pressure regulating means 80. At Step SA5, the three switch valves 30, 46, 58 are switched to their quick-deflation positions, so that the respective air pressures of the three cuffs 24, 40, 52 are quickly decreased.

Step SA5 is followed by Step SA6 corresponding to the cuff-pressure regulating means 80. At Step SA6, the two switch valve 30, 46 connected to the two cuffs 24, 40 respectively wound around the right and left ankles 12, 16, are switched, for determining the right and left pulse-wave propagation times $DT_R$, $DT_L$, to their pressure-supply positions, so that the respective air pressures $P_{C1}$, $P_{C2}$ of the two cuffs 24, 40 are increased up to a predetermined target value which is estimated to be sufficiently lower than the diastolic BP value of the patient, and then are maintained at the target value.

Step SA6 is followed by Step SA7 to judge, based on the ECG signal $SM_4$ supplied from the ECG 72, whether the ECG 72 has detected the R wave of a heartbeat-synchronous pulse of the ECG waveform. If a negative judgment is made at Step SA7, Step SA7 is repeated. Meanwhile, if a positive judgment is made, the control of the control device 38 goes to Step SA8 to judge, based on the pulse-wave signal $SM_1$ supplied from the pulse-wave filter circuit 36 of the right-ankle BP measuring device 14, whether the filter circuit 36 has detected the rising point of a heartbeat-synchronous pulse of the right-posterior-tibial-artery waveform.

If a negative judgment is made at Step SA8, the control skips Step SA9 and carries out Step SA10. Meanwhile, if a positive judgment is made at Step SA8, the control of the control device 38 goes to Step SA9 corresponding to the right PWV-relating-information obtaining means 88. At Step SA9, the control device 38 calculates, as shown in FIG. 3, a time difference between a time when the R wave is detected by the ECG 72 and a time when the rising point of the right-posterior-tibial-artery waveform is detected, i.e., a right pulse-wave propagation time $DT_R$ that is a time needed for a pulse wave to propagate from the heart to the portion of the right inferior limb (i.e., the right leg) around which the cuff 24 is wound.

At the following Step SA10, the control device 38 judges, based on the pulse-wave signal $SM_2$ supplied from the pulse-wave filter circuit 50 of the left-ankle BP measuring device 18, whether the filter circuit 50 has detected the rising point of a heartbeat-synchronous pulse of the left-posterior-tibial-artery waveform. If a negative judgment is made at Step SA10, the control skips Step SA11 and carries out Step SA12. Meanwhile, if a positive judgment is made at Step SA10, the control of the control device 38 goes to Step SA11 corresponding to the left PWV-relating-information obtaining means 90. At Step SA11, the control device 38 calculates a time difference between a time when the R wave is detected by the ECG 72 and a time when the rising point of the left-posterior-tibial-artery waveform is detected, i.e., a left pulse-wave propagation time $DT_L$ that is a time needed for a pulse wave to propagate from the heart to the portion of the left inferior limb (i.e., the left leg) around which the cuff 40 is wound.

At the following Step SA12, the control device 38 judges whether the control device 38 has determined both the right and left pulse-wave propagation times $DT_R$, $DT_L$. If a negative judgment is made at Step SA12, Steps SA8 to SA12 are repeated. Meanwhile, if a positive judgment is made at Step SA12, the control of the control device 38 goes to Step SA13 corresponding to the cuff-pressure regulating means 80. At Step SA13, the two switch valves 30, 46 are switched to their quick-deflation positions, so that the respective air pressures of the two cuffs 24, 40 are quickly decreased.

Step SA13 is followed by Step SA14 corresponding to the BP selecting means 92. At Step SA14, the control device 38 compares the right and left pulse-wave propagation times $DT_R$, $DT_L$ determined at Step SA9, with each other, and selects one of the right-ankle and left-ankle systolic BP values $BP_{RSYS}$, $BP_{LSYS}$ that corresponds to the longer one of the right and left pulse-wave propagation times $DT_R$, $DT_L$. The thus selected ankle systolic BP value is used in determining an API value at the next step.

Step SA14 is followed by Step SA15 corresponding to the ankle/arm BP index determining means 94. At Step SA15, the control device 38 calculates an API value by dividing the ankle systolic BP value selected at Step SA14, by the upper-arm systolic BP value $BP_{ASYS}$ determined at Step SA4. The thus determined API value is displayed on the display device 70.

As is apparent from the foregoing description, the right PWV-relating-information obtaining means 88 (Step SA9) obtains the right pulse-wave propagation time $DT_R$ needed for the pulse wave to propagate from the heart to the right ankle 12 around which the cuff 24 is wound; the left PWV-relating-information obtaining means 90 (Step SA11) obtains the left pulse-wave propagation time $DT_L$ needed for the pulse wave to propagate from the heart to the left ankle 16 around which the cuff 40 is wound; the BP selecting means 92 (Step SA14) selects one of the right-ankle and left-ankle systolic BP values that corresponds to the longer one of the right and left pulse-wave propagation times $DT_R$, $DT_L$. The thus selected ankle systolic BP value corresponds to one of the two inferior limbs (i.e., the two legs) that has been less calcified than the other. Since the selected ankle systolic BP value is used in determining the API value, the thus determined API value enjoys high reliability.

Next, there will be described a second embodiment of the present invention that relates to an ankle/arm BP index measuring apparatus 100. The present apparatus 100 differs from the apparatus 10, shown in FIG. 1, only in that the present apparatus 100 does not employ the ECG 72 and the electrodes 74 employed in the apparatus 10 and that an electronic control device 38 of the present apparatus 100 has different control functions. Accordingly, the same reference numerals as used in the first embodiment shown in FIGS. 1 to 4 are used to designate the corresponding elements and parts of the second embodiment shown in FIGS. 5 to 7, and the description thereof is omitted.

Figure 5:
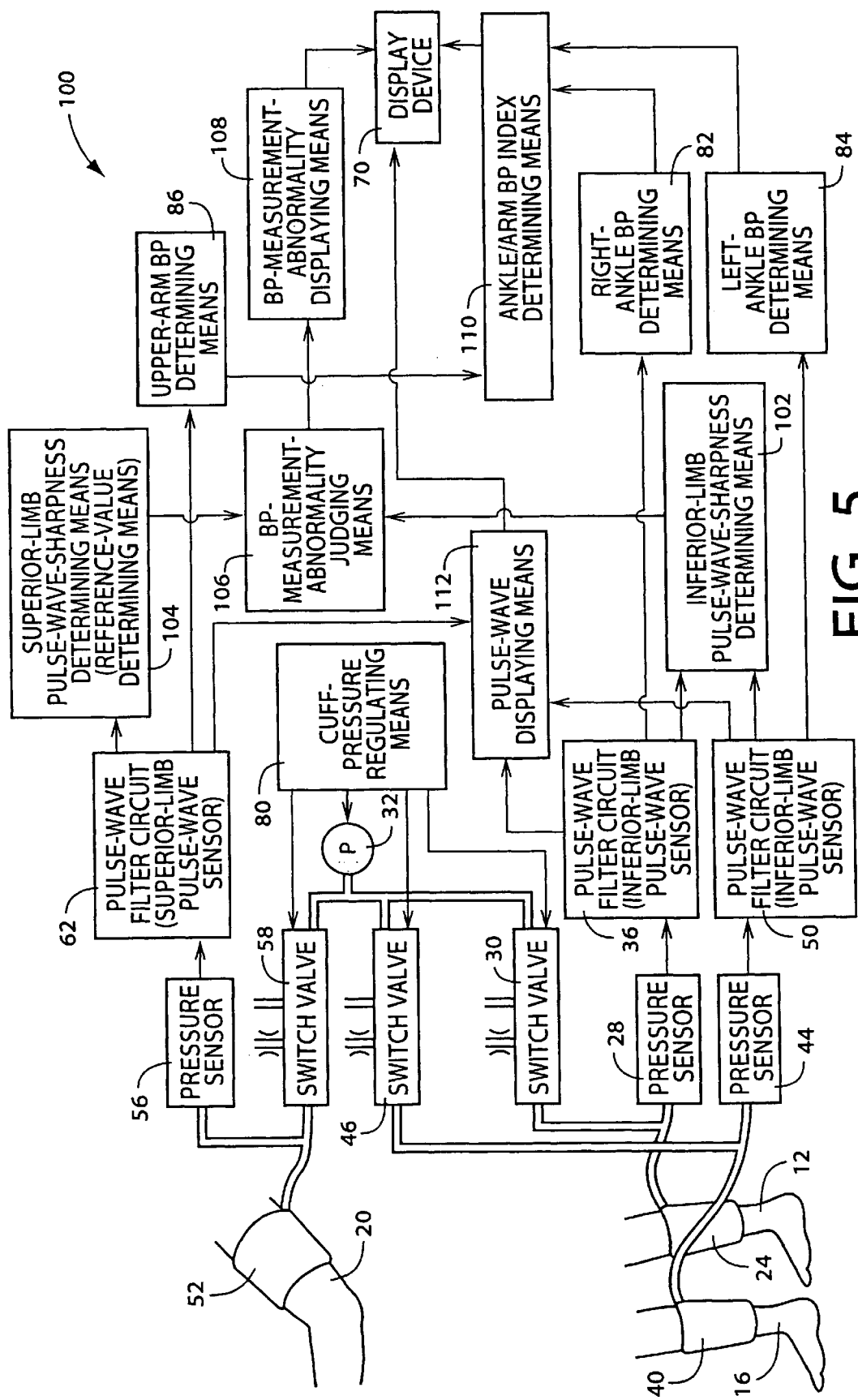
FIG. 5 is a diagrammatic view of important control functions of an electronic control device of an ankle/arm BP index measuring apparatus as a second embodiment of the present invention.

FIG. 5 is a diagrammatic view for explaining important control functions of the control device 38.

An inferior-limb pulse-wave-sharpness determining means 102 determines a degree of sharpness of a heartbeat-synchronous pulse of a first inferior-limb pulse wave detected by a first inferior-limb pulse-wave sensor worn on an upstream-side portion of the right inferior limb that is located on an upstream side of the cuff 24 wound around the right ankle 12 (the upstream-side portion of the right inferior limb may be a portion thereof around which the cuff 24 is wound), and additionally determines a degree of sharpness of a heartbeat-synchronous pulse of a second inferior-limb pulse wave detected by a second inferior-limb pulse-wave sensor worn on an upstream-side portion of the left inferior limb that is located on an upstream side of the cuff 40 wound around the left ankle 16 (the upstream-side portion of the left inferior limb may be a portion thereof around which the cuff 40 is wound). The pulse-wave filter circuit 36 connected to the cuff 24 via the pressure sensor 28 functions as the first inferior-limb pulse-wave sensor, and the second pulse-wave filter circuit 50 connected to the cuff 40 via the pressure sensor 44 functions as the second inferior-limb pulse-wave sensor. The inferior-limb pulse-wave-sharpness determining means 102 determines a degree of sharpness of a heartbeat-synchronous pulse of the pulse wave detected from the right posterior tibial artery by the filter circuit 36, and determines a degree of sharpness of a heartbeat-synchronous pulse of the pulse wave detected from the left posterior tibial artery by the filter circuit 50. The degree of sharpness means a degree of sharpness of upward projection of a heartbeat-synchronous pulse. For example, the degree of sharpness may be an index, %MAP, which is defined as a percentage of a height, a, of a center of gravity of an area enveloped by a heartbeat-synchronous pulse, relative to an amplitude, b, of the pulse. The height a indicates a mean BP value, MAP, and the amplitude b indicates a pulse pressure obtained by subtracting a diastolic BP value from a systolic BP value. That is, the index %MAP is obtained according to the following expression (3):

$$\%MAP = 100 \times a/b \quad (3)$$

A superior-limb pulse-wave-sharpness determining means 104 determines a degree of sharpness of a heartbeat-synchronous pulse of a superior-limb pulse wave detected by a superior-limb pulse-wave sensor worn on an upstream-side portion of the superior limb that is located on an upstream side of the cuff 52 wound around the upper arm 20 (the upstream-side portion of the superior limb may be a portion thereof around which the cuff 52 is wound). The pulse-wave filter circuit 62 connected to the cuff 52 via the pressure sensor 56 functions as the superior-limb pulse-wave sensor, and the superior-limb pulse-wave-sharpness determining means 104 determines, like the means 102, a degree of sharpness of a heartbeat-synchronous pulse of the upper-arm pulse wave detected by the filter circuit 62.

A BP-measurement-abnormality judging means 106 judges that when the degree of sharpness of the right-posterior-tibial-artery pulse wave determined by the means 102 is not greater than a reference value, TH, and the measured right-ankle BP value $BP_L$ is higher than the measured corresponding upper-arm BP value $BP_A$ by a value not smaller than a reference value, α, the BP determination of the right-ankle BP determining means 82 is abnormal, and judges that when the degree of sharpness of the left-posterior-tibial-artery pulse wave determined by the means 102 is not greater than the reference value TH, and the measured left-ankle BP value $BP_L$ is higher than the measured corresponding upper-arm BP value $BP_A$ by a value not smaller than the reference value α, the BP determination of the left-ankle BP determining means 84 is abnormal. The reference value TH may be a constant value which is determined based on a normal degree of sharpness of a pulse of posterior-tibial-artery pulse wave. However, since, for a person who does not suffer inferior-limb arterial stenosis, a degree of sharpness of posterior-tibial-artery pulse wave is greater than that of brachial-artery pulse wave, the degree of sharpness of the upper-arm pulse wave determined by the means 104 may be used as the reference value TH. In the latter case, the superior-limb pulse-wave-sharpness determining means 104 functions as a reference-value determining means. The reference value α is experimentally determined in advance, and a value about 10 mmHg may be employed as the value a.

A BP-measurement-abnormality displaying means 108 controls, if the BP-measurement-abnormality judging means 106 judges that the BP determination of the right-ankle BP determining means 82 is abnormal, and/or that the BP determination of the left-ankle BP determining means 84 is abnormal, the display device 70 to display characters or symbols indicating that the BP determination of the right-ankle BP determining means 82 is abnormal and/or that the BP determination of the left-ankle BP determining means 84 is abnormal.

An ankle/arm BP index determining means 110 determines a right ankle/arm BP index value (=$API_R$) based on the right-ankle BP value $BP_R$ determined by the means 82 and the upper-arm BP value $BP_A$ (corresponding to the right-ankle BP value $BP_R$) determined by the means 86, and determines a left ankle/arm BP index-value (=$API_L$) based on the left-ankle BP value $BP_L$ determined by the means 84 and the upper-arm BP value $BP_A$.

A pulse-wave displaying means 112 controls the display device 70 to display, together with the right-ankle BP value $BP_R$, the left-ankle BP value $BP_L$, and the upper-arm BP value $BP_A$, respective waveforms of the right-posterior-tibial-artery pulse wave, the left-posterior-tibial-artery pulse wave, and the brachial-artery pulse-wave which are respectively detected by the pulse-wave filter circuits 36, 50, 62 in a state in which the respective air pressures $P_{C1}$, $P_{C2}$, $P_{C3}$ of the three cuffs 24, 40, 52 are held at a pressure value sufficiently lower than the diastolic BP value of the patient.

Figure 6:
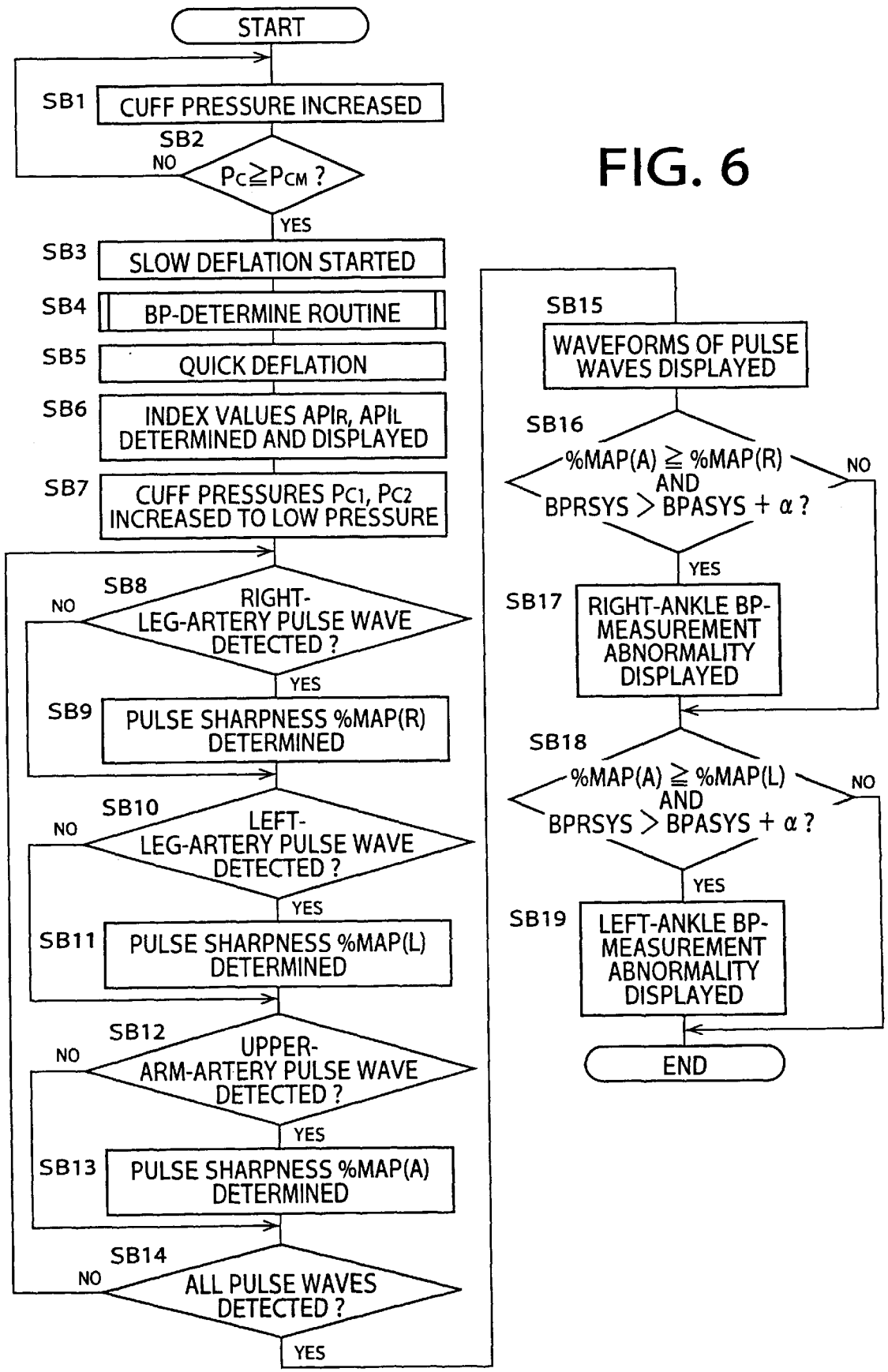
FIG. 6 is a flow chart representing a control program according to which the control device of the measuring apparatus of FIG. 5 is operated.

FIG. 6 is a flow chart representing a control program according to which the control device 38 of the ankle/arm BP index measuring apparatus 100 is operated. In FIG. 6, Steps SB1 to SB5 are identical with Steps SA1 to SA5 of the flow chart, shown in FIG. 4, which is employed in the first embodiment. Thus, the apparatus 100 determines a right-ankle systolic BP value $BP_{RSYS}$, a left-ankle systolic BP value $BP_{LSYS}$, and an upper-arm systolic BP value $BP_{ASYS}$, and deflates the respective air pressures $P_{C1}$, $P_{C2}$, $P_{C3}$ of the three cuffs 24, 40, 52.

Figure 7:
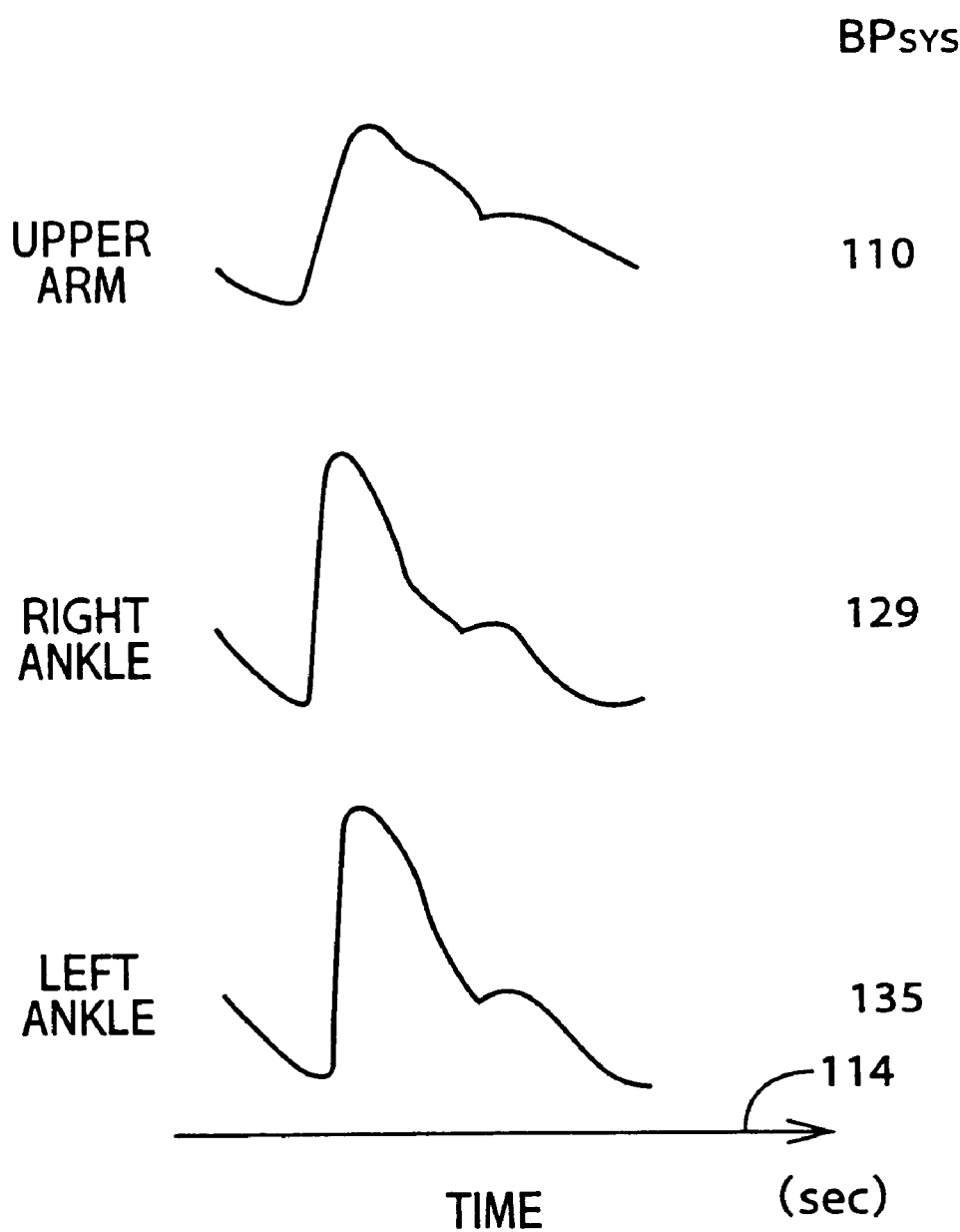
FIG. 7 is a view showing an example of a screen image displayed by a display device of the measuring apparatus of FIG. 5.

Step SB5 is followed by Step SB6 corresponding to the ankle/arm BP index determining means 110. At Step SB6, the control device 38 determines an index value $API_R$ by dividing the right-ankle systolic BP value $BP_{RSYS}$ determined at Step SB4 by the upper-arm systolic BP value $BP_{ASYS}$ determined at the same step, and determines an index value $API_L$ by dividing the left-ankle systolic BP value $BP_{LSYS}$ determined at Step SB4 by the upper-arm systolic BP value $BP_{ASYS}$. The thus determined index values $API_R$, $API_L$ are displayed on the display device 70, as shown in FIG. 7.

Subsequently, the control device 38 judges whether the measurement of the right-ankle BP values and/or the measurement of the left-ankle BP values are or is abnormal.

First, at Step SB7 corresponding to the cuff-pressure regulating means 80, the three switch valves 30, 46, 58 are switched to their pressure-supply states, so that the respective air pressures $P_{C1}$, $P_{C2}$, $P_{C3}$ of the three cuffs 24, 40, 52 are increased up to a predetermined pressure value sufficiently lower than the diastolic BP value of the patient, and then are maintained at that value.

At the following Step SB8, the control device 38 judges, based on the pulse-wave signal $SM_1$ supplied from the pulse-wave filter circuit 36, whether the filter circuit 36 has detected a waveform corresponding to one heartbeat-synchronous pulse of the right-posterior-tibial-artery pulse wave. If a negative judgment is made at Step SB8, the control skips Step SB9 and proceeds with Step SB10. On the other hand, if a positive judgment is made at Step SB8, the control goes to Step SB9 corresponding to the inferior-limb pulse-wave-sharpness determining means 102. At Step SB9, the control device 38 determines a height, a, of a center of gravity of an area enveloped by the waveform of the one heartbeat-synchronous pulse wave detected at Step SB8, and additionally determines an amplitude, b, of the waveform of the one pulse. Based on the thus determined height a and amplitude b, the control device 38 determines a sharpness degree, %MAP(R), of the right-posterior-tibial-artery pulse wave. Step SB9 is followed by Step SB10.

At Step SB10, the control device 38 carries out an identical operation on the left ankle 16. That is, the control device 38 judges, based on the pulse-wave signal $SM_2$ supplied from the pulse-wave filter circuit 50, whether the filter circuit 50 has detected a waveform corresponding to one heartbeat-synchronous pulse of the left-posterior-tibial-artery pulse wave. If a negative judgment is made at Step SB10, the control skips Step SB11 and proceeds with Step SB12. On the other hand, if a positive judgment is made at Step SB10, the control goes to Step SB11 corresponding to the inferior-limb pulse-wave-sharpness determining means 102. At Step SB11, the control device 38 determines a height a of a center of gravity of an area enveloped by the waveform of the one heartbeat-synchronous pulse wave detected at Step SB10, and additionally determines an amplitude b of the waveform of the one pulse. Based on the thus determined height a and amplitude b, the control device 38 determines a sharpness degree, %MAP(L), of the left-posterior-tibial-artery pulse wave. Step SB11 is followed by Step SB12.

At Step SB12, the control device 38 carries out an identical operation on the upper arm 20. That is, the control device 38 judges, based on the pulse-wave signal $SM_3$ supplied from the pulse-wave filter circuit 62, whether the filter circuit 62 has detected a waveform corresponding to one heartbeat-synchronous pulse of the brachial-artery pulse wave. If a negative judgment is made at Step SB12, the control skips Step SB13 and proceeds with Step SB14. On the other hand, if a positive judgment is made at Step SB12, the control goes to Step SB13 corresponding to the superior-limb pulse-wave-sharpness determining means 104. At Step SB13, the control device 38 determines a height a of a center of gravity of an area enveloped by the waveform of the one heartbeat-synchronous pulse wave detected at Step SB12, and additionally determines an amplitude b of the waveform of the one pulse. Based on the thus determined height a and amplitude b, the control device 38 determines a sharpness degree, %MAP(A), of the brachial-artery pulse wave. Step SB13 is followed by Step SB14.

At Step SB14, the control device 38 judges whether the three filter circuits 36, 50, 62 have detected respective waveforms corresponding to respective one heartbeat-synchronous pulses of the right-posterior-tibial-artery pulse wave, the left-posterior-tibial-artery pulse wave, and the brachial-artery pulse wave. If a negative judgment is made at Step SB14, the control goes back to Step SB8 and the following steps. On the other hand, if a positive judgment is made at Step SB14, the control goes to Step SB15 corresponding to the pulse-wave displaying means 112. At Step SB15, the control device 38 controls the display device 70 to display, together with the right-ankle systolic BP value $BP_{RSYS}$, the left-ankle systolic BP value $BP_{LSYS}$, and the upper-arm systolic BP value $BP_{ASYS}$ displayed at Step SB4, the waveform of the right-posterior-tibial-artery pulse wave, the waveform of the left-posterior-tibial-artery pulse wave, and the waveform of the brachial-artery pulse wave, each along a time axis 114, as shown in FIG. 7. FIG. 7 shows an example of the three BP values $BP_{RSYS}$, $BP_{LSYS}$, $BP_{ASYS}$ displayed at Step SB4, the two index values $API_R$, $API_L$ displayed at Step SB6, and the three pulse-wave waveforms displayed at Step SB15. The display device 70 displays, alon the time axis 114, the three pulse-wave waveforms, side by side, so that an observer can compare those waveforms with one another.

Step SB15 is followed by Step SB16 corresponding to the BP-measurement-abnormality judging means 106. At Step SB16, the control device 38 judges whether the degree of sharpness %MAP (R) of the right-posterior-tibial-artery pulse wave determined at Step SB9 is not greater than the degree of sharpness %MAP (A) of the brachial-artery pulse wave determined at Step SB13 and simultaneously the right-ankle systolic BP value $BP_{RSYS}$ determined at Step SB4 is higher than a sum of the upper-arm systolic BP value $BP_{ASYS}$ determined at Step SB4 and the reference value α. If a positive judgment is made, the control device 38 concludes that in the BP measurement carried out for the right ankle 12, the flow of blood was not completely stopped by the pressing of the inflatable cuff 24, and therefore that the BP measurement was abnormal. Step SB16 is followed by Step SB17 corresponding to the BP-measurement-abnormality displaying means 108. At Step SB17, the control device 38 controls the display device 70 to display characters and/or symbols indicating that the BP measurement carried out for the right ankle 12 was abnormal.

If a negative judgment is made at Step SB16, or after Step SB17, the control goes to Step SB18 corresponding to the BP-measurement-abnormality judging means 106. At Step SB18, the control device 38 judges whether the degree of sharpness %MAP (L) of the left-posterior-tibial-artery pulse wave determined at Step SB11 is not greater than the degree of sharpness %MAP (A) of the brachial-artery pulse wave determined at Step SB13 and simultaneously the left-ankle systolic BP value $BP_{LSYS}$ determined at Step SB4 is higher than a sum of the upper-arm systolic BP value $BP_{ASYS}$ and the reference value α. If a positive judgment is made, the control device 38 concludes that in the BP measurement carried out for the left ankle 16, the flow of blood was not completely stopped by the pressing of the inflatable cuff 40, and therefore that the BP measurement was abnormal. Step SB18 is followed by Step SB19 corresponding to the BP-measurement-abnormality displaying means 108. At Step SB19, the control device 38 controls the display device 70 to display characters and/or symbols indicating that the BP measurement carried out for the left ankle 16 was abnormal. If a negative judgment is made at Step SB18, or after Step SB19, the control device 38 quits the present control routine represented by the flow chart of FIG. 6.

As is apparent from the foregoing description, in the second embodiment, the inferior-limb pulse-wave sharpness determining means 102 (Step SB9) determines the sharpness %MAP(R) of the right-posterior-tibial-artery pulse wave detected by the pulse-wave filter circuit 36, and the BP-measurement abnormality judging means 106 (Step SB16) judges that when the pulse-wave sharpness %MAP (R) determined by the means 102 is not greater than the sharpness %MAP(A) of the brachial-artery pulse wave and the right-ankle systolic BP value $BP_{RSYS}$ is higher than the upper-arm systolic BP value $BP_{ASYS}$ by a value not smaller than the reference value α, the BP measurement carried out by the right-ankle BP measuring device 14 for the right ankle 12 is abnormal. Thus, an observer or an operator such as a medical staff can know that the BP measurement carried out for the right ankle 12 has not been properly carried out.

In addition, in the second embodiment, the inferior-limb pulse-wave sharpness determining means 102 (Step SB11) determines the sharpness %MAP(L) of the left-posterior-tibial-artery pulse wave detected by the pulse-wave filter circuit 50, and the BP-measurement absnormality judging means 106 (Step SB18) judges that when the pulse-wave sharpness %MAP(L) determined by the means 102 is not greater than the sharpness %MAP(A) of the brachial-artery pulse wave and the left-ankle systolic BP value $BP_{LSYS}$ is higher than the upper-arm systolic BP value $BP_{ASYS}$ by a value not smaller than the reference value α, the BP measurement carried out for the left ankle 16 is abnormal. Thus, an observer or an operator such as a medical staff can know that the BP measurement carried out for the left ankle 16 has not been properly carried out.

Moreover, in the second embodiment, the display device 70 simultaneously displays the right-ankle and left-ankle systolic BP values $BP_{RSYS}$, $BP_{LSYS}$ and the upper-arm systolic BP value $BP_{ASYS}$, and the respective waveforms of the right and left posterior-tibial-artery pulse waves and the brachial-artery pulse wave. Therefore, in the case where the right-ankle systolic BP value $BP_{RSYS}$ is higher than the upper-arm systolic BP value $BP_{ASYS}$, but the waveform of the right posterior-tibial-artery pulse wave is less sharp than that of the brachial-artery pulse wave, an observer can judge that the BP measurement carried out by the right-ankle BP measuring device 14 for the right ankle 12 is abnormal and, in the case where the left-ankle systolic BP value $BP_{LSYS}$ is higher than the upper-arm systolic BP value $BP_{ASYS}$, but the waveform of the left posterior-tibial-artery pulse wave is less sharp than that of the brachial-artery pulse wave, the observer can judge that the BP measurement carried out by the left-ankle BP measuring device 18 for the left ankle 16 is abnormal.

Figure 8:
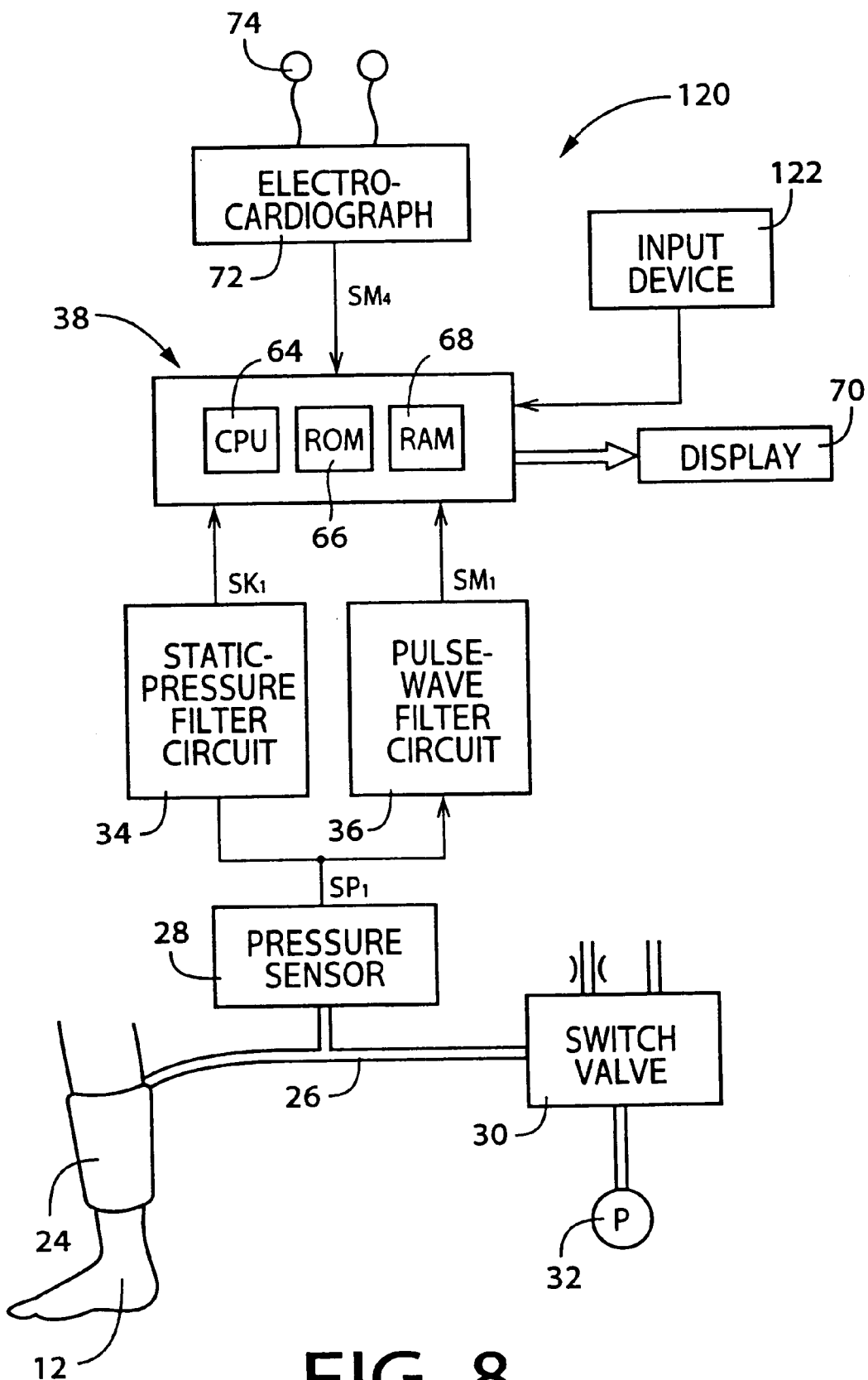
FIG. 8 is a diagrammatic view of the construction of an ankle/arm BP index measuring apparatus as the third embodiment of the present invention.

Next, there will be described a third embodiment of the present invention that relates to an inferior-limb-BP measuring apparatus 120. FIG. 8 is a diagrammatic view for explaining the construction of the present apparatus 120. The same reference numerals as used in the first embodiment shown in FIGS. 1 to 4 are used to designate the corresponding elements and parts of the third embodiment shown in FIGS. 8 to 11, and the description thereof is omitted.

In short, the inferior-limb BP measuring apparatus 120 includes an inflatable cuff 24, a piping 26, a pressure sensor 28, a switch valve 30, an air pump 32, a static-pressure filter circuit 34, a pulse-wave filter circuit 36, an ECG 72, and electrodes 74 which have respective constructions identical with those of the corresponding elements 24, 26, 28, 30, 32, 34, 36 72, 74 employed in the first embodiment. The cuff 24 is wound around a right ankle 12 of a living subject or a patient, to measure a right-ankle BP value of the patient. The present apparatus additionally includes a control device 38 including a CPU 64, a ROM 66, and a RAM 68, and a display device 70.

Moreover, an input device 122 includes a keyboard (not shown) which is manually operable by an operator for inputting at least one value characteristic of the patient, and which produces at least one signal, SC, representing the input at least one characteristic value and supplies the signal SC to the control device 38. The one or more characteristic values may include the age, sex, height, etc. of the patient. Those characteristic values are physical information which influences a relationship between blood pressure and information relating to velocity of propagation of pulse wave. One or more predetermined items are input as the one or more characteristic values.

Figure 9:
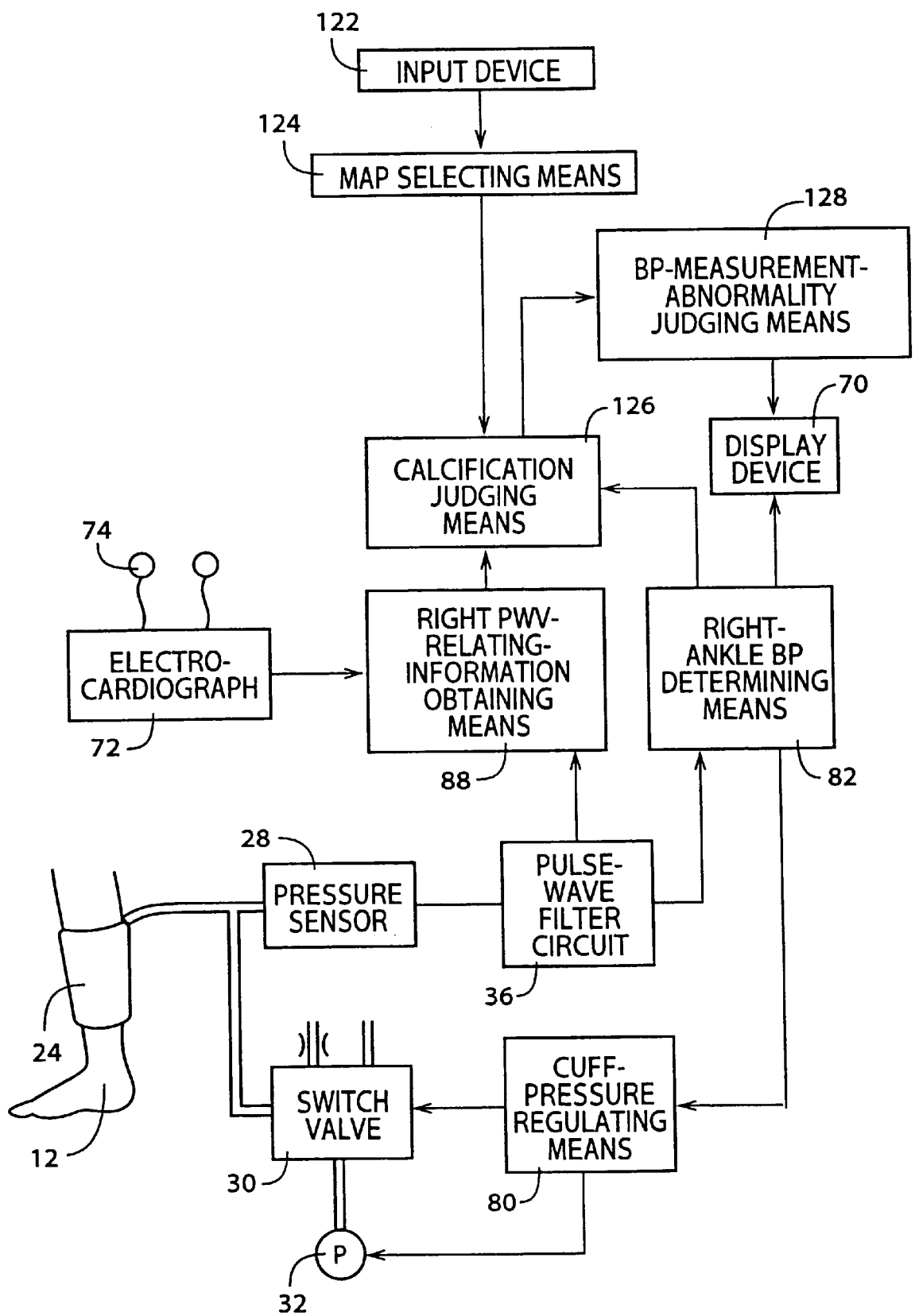
FIG. 9 is a diagrammatic view of important control functions of an electronic control device of the measuring apparatus of FIG. 8.

FIG. 9 is a diagrammatic view for explaining important control functions of the control device 38 of the inferior-limb-BP measuring apparatus 120.

Figure 10:
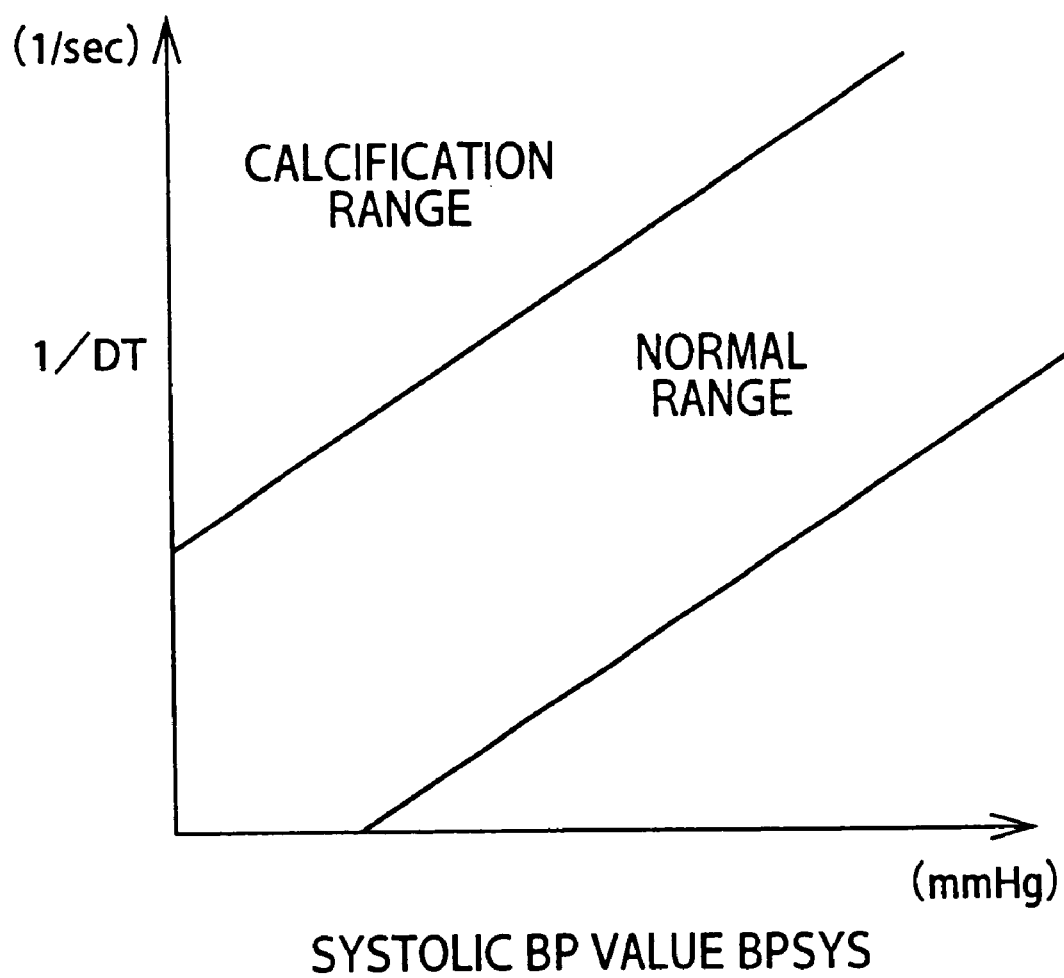
FIG. 10 is a view showing an example of a map selected by a map selecting means of the measuring device of FIG. 8.

A map selecting means 124 selects, based on the signal SC supplied from the input device 122, one of a plurality of predetermined maps which correspond to a plurality of predetermined ranges for the input characteristic value, respectively, which are stored in the ROM 66, and each of which indicates, in a graph defined by a first axis representing blood pressure BP and a second axis representing information relating to velocity of propagation of pulse wave through arterial vessel, a calcification range which is experimentally determined in advance and indicates that the arterial vessel has been calcified. FIG. 10 shows an example of the maps stored in the ROM 66 and selected by the map selecting means 124. The map of FIG. 10 indicates, in a graph defined by a first axis representing systolic blood pressure BPSYS and a second axis representing inverse, 1/DT, of propagation time, DT, of pulse wave, a normal range and a calcification range. At the same BP value, the velocity of propagation of a pulse wave which propagates through a calcified artery is higher than that of a pulse wave which propagates through a non-calcified artery. That is, at the same BP value, the inverse 1/DT of the propagation time DT of the pulse wave which propagates through the calcified artery is greater than that of the pulse wave which propagates through the non-calcified artery. Therefore, in the map shown in FIG. 10, the calcification range is located above the normal range.

A calcification judging means 126 judges whether the right-ankle BP value measured by the right-ankle BP determining means 82 and the right PWV-relating information obtained by the right PWV-relating-information obtaining means 88 fall in the calcification range of the selected map and, if a positive judgment is made, judges that at least one blood vessel running in the right ankle 12 around which the cuff 24 is wound has been calcified to such a degree that the blood vessel cannot be fully or completely occluded by the pressing of the cuff 24, that is, the blood flow cannot be fully stopped by the cuff 24.

A BP-measurement-abnormality displaying means 128 controls, if the calcification judging means 126 judges that the blood vessels running in the right ankle 12 around which the cuff 24 is wound have been calcified to such a degree that the blood vessels cannot be fully occluded by the cuff 24, the display device 70 to display characters and/or symbols indicating that the BP measurement carried out for the right ankle 12 is abnormal.

Figure 11:
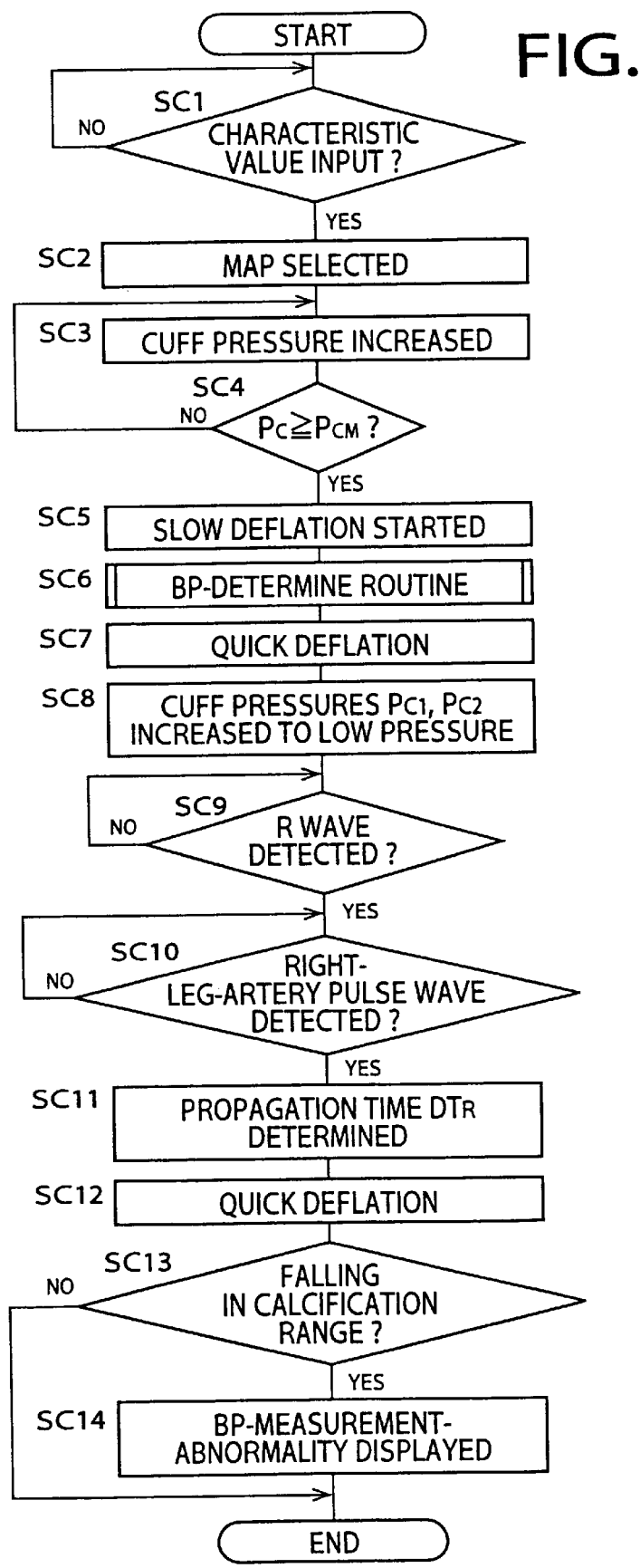
FIG. 11 is a flow chart representing a control program according to which the control device of the measuring apparatus of FIG. 8 is operated.

FIG. 11 is a flow chart representing a control program according to which the control device 38 of the inferior-limb-BP measuring apparatus 120 is operated.

First, at Step SC1, the control device 38 judges whether the control device 38 has received, from the input device 122, the signal SC representing the characteristic value of the patient, and thereby judges whether the characteristic value has been input by the operator.

If a negative judgment is made at Step SC1, Step SC1 is repeated. Meanwhile, if a positive judgment is made at Step SC1, the control of the control device 38 goes to Step SC2 corresponding to the map selecting means 124. At Step SC2, the control device 38 selects, based on the signal SC supplied from the input device 122, one of the predetermined maps stored in the ROM 66.

Steps SC3 to SC11 are identical with Steps SA1 to SA9 of the flow chart, shown in FIG. 4, which is employed in the first embodiment. Thus, the present apparatus 120 measures right-ankle systolic and diastolic BP values $BP_{RSYS}$, $BP_{RDIA}$, etc., and maintains the air pressure $P_{C1}$ of the cuff 24 at a predetermined pressing pressure value sufficiently lower than the diastolic BP value of the patient. In this state, the control device 38 measures a right pulse-wave propagation time, $DT_R$, needed for a pulse wave to propagate from the heart to the right ankle 12.

Step SC11 is followed by Step SC12 to switch the switch valve 30 to its quick-deflation position, thereby quickly decreasing the air pressure of the cuff 24.

Step SC12 is followed by Step SC13 corresponding to the calcification judging means 126. At Step SC13, the control device 38 judges whether the right-ankle systolic BP value determined at Step SC6 and the right pulse-wave propagation time $DT_R$ determined at Step SC11 fall in the calcification range of the map selected at Step $SC_2$.

If a negative judgment is made at Step SC13, the control device 38 quits the present control routine. On the other hand, if a positive judgment is made at Step SC13, the control of the control device 38 goes to Step SC14 corresponding to the BP-measurement-abnormality displaying means 128. At Step SC14, the control device 38 controls the display device 70 to display characters and/or symbols indicating that the BP measurement carried out for the right ankle 12 is abnormal. After Step SC14, the control device 38 quits this control routine.

As is apparent from the foregoing description, in the third embodiment, the map selecting means 124 (Step $SC_2$) selects, based on the characteristic value input through the input device 122, one of the plurality of predetermined maps each of which indicates the calcification range in the graph defined by the first axis representing right-ankle systolic blood pressure $BP_{RSYS}$ and the second axis representing pulse-wave propagation time $DT_R$. The calcification judging means 126 (Step SC13) judges whether the measured right-ankle systolic BP value $BP_{RSYS}$ and the measured pulse-wave propagation time $DT_R$ fall in the calcification range of the map selected by the map selecting means 124, and thereby judges whether the arterial vessels running in the right ankle around which the cuff 24 is wound have been calcified to such an extent that the blood flow cannot be stopped by the cuff 24. Thus, the judging means 126 judges whether the BP measurement carried out for the right ankle 12 is abnormal.

While the present invention has been described in its preferred embodiments, it may be otherwise embodied.

For example, in the illustrated embodiment, the ECG (electrocardiograph) 72 is used as the first pulse-wave sensor commonly for obtaining both the right and left PWV-relating information. However, the ECG 72 may be replaced with a microphone which is worn on the chest of the living subject and detects respective heart sounds produced when the heart starts and ending outputting blood toward the aorta.

In addition, each first pulse-wave sensor, such as the pulse-wave filter circuit 62 connected to the cuff 52 wound around the upper arm 20 via the pressure sensor 52, may be provided by a pulse-wave sensor which detects a pulse wave from a portion of the subject that is more distant from the corresponding second pulse-wave sensor than the heart of the subject.

Moreover, the two (right and left) first pulse-wave sensors may be provided by two pulse-wave sensors which are adapted to be worn on respective femoral portions of two legs of the subject.

The two (right and left) second pulse-wave sensors may be provided by two peripheral-pulse-wave sensors which are adapted to be worn on respective one toes of two feet of the subject.

In the illustrated embodiment, each of the right-ankle BP measuring device 14, the left-ankle BP measuring device 18, and the upper-arm BP measuring device 22 measures a BP value according to the oscillometric method. However, each of the three BP measuring devices 14, 18, 22 may be one which measures a BP value according to a well-known Korotkoff-sound method in which a BP value is measured based on a cuff-pressure value read at a time when Korotkoff sounds are first or last detected. Otherwise, each device 14, 18, 22 may be one which measures a BP value according to a supersonic Doppler method in which, while a pressure which presses an artery is changed, a supersound emitter and a supersound receiver which are provided right above the artery cooperate with each other to detect the opening and closing of the arterial vessel.

Each of the three BP measuring devices 14, 18, 22 of the first embodiment and the upper-arm BP measuring device 22 of the second embodiment may be provided by a BP measuring device which does not employ any inflatable cuffs, such as an invasive BP measuring device which invasively measures a BP value of a subject.

The ankle/arm BP index measuring apparatus 10, 110 is a sort of superior-and-inferior-limb BP index measuring apparatus wherein an ankle is selected as an inferior limb and an upper arm is selected as a superior limb, and the inferior-limb BP measuring apparatus 120 measures a BP value from an ankle as an inferior limb. However, a femoral portion or a toe may be selected as an inferior limb, and a wrist or a finger may be selected as a superior limb.

In the second embodiment, the two inferior-limb pulse-wave sensors are provided by the two pulse-wave filter circuits 36, 50, respectively, which detect the respective pulse waves from the respective portions of the two inferior limbs around which the two cuffs 24, 40 are wound. However, the inferior-limb pulse-wave sensors may be worn on respective upstream-side portions of the two inferior limbs that are located on respective upstream sides of the two cuffs 24, 40 as seen in respective directions in which arterial blood flows in the inferior limbs. Similarly, although in the second embodiment the superior-limb pulse wave sensor is provided by the pulse-wave filter circuit 62 which detects the brachial-artery pulse wave, the superior-limb pulse-wave sensor may be provided by a pulse-wave sensor which is adapted to be worn on a wrist or a finger.

In the third embodiment, the control device 38 obtains information relating to velocity of propagation of pulse wave which propagates from the heart to the ankle 12 around which the cuff 24 is wound. However, two pulse-wave sensors may be worn on both sides of the cuff 24, and respective pulse waves detected by the two sensors may be used to obtain information relating to velocity of propagation of pulse wave. For example, in the case where a cuff is wound around an ankle of a leg, two pulse-wave sensors may be worn on a femoral portion and a toe of the same leg, respectively, to obtain information relating to velocity of propagation of pulse wave which propagates from the femoral portion to the toe. In the latter case, the apparatus 120 can more accurately judge whether the blood vessels of the body portion around which the cuff is wound have been calcified.

In the third embodiment, the apparatus 120 measures a BP value from the right ankle 12. However, the apparatus may measure a BP value from a left ankle.

It is to be understood that the present invention may be embodied with other changes, improvements, and modifications that may occur to a person skilled in the art without departing from the scope and spirit of the invention defined in the appended claims.

What is claimed is:

1. An apparatus for measuring a blood pressure of an inferior limb of a living subject, comprising:

a blood-pressure measuring device which includes an inflatable cuff adapted to be wound around the inferior limb and which measures, with the cuff, the blood pressure of the inferior limb of the subject;

an input device which is operable for inputting at least one characteristic value characteristic of the subject and which produces at least one signal representing the at least one input characteristic value;

map selecting means for selecting, based on the input characteristic value, one of a plurality of predetermined maps each of which defines, in a coordinate system having a first axis representing blood pressure and a second axis representing information relating to velocity of propagation of pulse wave through blood vessel, a calcification range indicating calcification of the blood vessel;

an information obtaining device which obtains information relating to a velocity of propagation of a pulse wave which propagates between two different portions of the subject that include a portion of the inferior limb around which the inflatable cuff is wound; and judging means for judging whether the measured blood pressure and the obtained information fall in the calcification range of the selected map, and thereby judging whether at least one blood vessel running in said portion of the inferior limb has been calcified to such a degree that a blood flow through the blood vessel cannot be stopped by the inflatable cuff.

2. An apparatus according to claim 1, wherein the input device comprises means for inputting, as the at least one characteristic value, at least one value selected from the group consisting of an age of the subject, a value corresponding to a sex of the subject, and a height of the subject.

3. An apparatus according to claim 1, further comprising a memory which stores the plurality of predetermined maps.

4. An apparatus according to claim 1, wherein the information obtaining device comprises propagation-time measuring means for measuring a time needed for the pulse wave to propagate between the two different portions of the subject.

5. An apparatus according to claim 4, wherein the information obtaining device further comprises inverse-of-propagation-time determining means for determining, as said information, an inverse of the propagation time measured by the propagation-time measuring means.

* * * * *